United States Patent
Buchanan et al.

(10) Patent No.: US 10,077,305 B2
(45) Date of Patent: Sep. 18, 2018

(54) ANTIBODIES AGAINST PD-1 AND USES THEREOF

(71) Applicant: MedImmune Limited, Cambridge (GB)

(72) Inventors: Andrew G. Buchanan, Cambridge (GB); Ross Stewart, Cambridge (GB); Mathieu Chodorge, Cambridge (GB)

(73) Assignee: MedImmune Limited, Cambridge (GB)

( * ) Notice: Subject to any disclaimer, the term of this patent is extended or adjusted under 35 U.S.C. 154(b) by 233 days.

(21) Appl. No.: 15/021,088

(22) PCT Filed: Sep. 9, 2014

(86) PCT No.: PCT/EP2014/069170
§ 371 (c)(1),
(2) Date: Mar. 10, 2016

(87) PCT Pub. No.: WO2015/036394
PCT Pub. Date: Mar. 19, 2015

(65) Prior Publication Data
US 2016/0222113 A1   Aug. 4, 2016

Related U.S. Application Data

(60) Provisional application No. 61/875,847, filed on Sep. 10, 2013.

(51) Int. Cl.
*C07K 16/28* (2006.01)
*A61K 39/395* (2006.01)
*G01N 33/68* (2006.01)

(52) U.S. Cl.
CPC ...... *C07K 16/2803* (2013.01); *C07K 16/2818* (2013.01); *G01N 33/6854* (2013.01); *C07K 2317/21* (2013.01); *C07K 2317/53* (2013.01); *C07K 2317/54* (2013.01); *C07K 2317/55* (2013.01); *C07K 2317/56* (2013.01); *C07K 2317/565* (2013.01); *C07K 2317/569* (2013.01); *C07K 2317/622* (2013.01); *C07K 2317/76* (2013.01); *C07K 2317/92* (2013.01); *G01N 2333/70503* (2013.01)

(58) Field of Classification Search
None
See application file for complete search history.

(56) References Cited

U.S. PATENT DOCUMENTS

| 7,488,802 B2* | 2/2009 | Collins | C07K 16/2803 424/130.1 |
|---|---|---|---|
| 7,521,051 B2* | 4/2009 | Collins | C07K 16/2803 424/130.1 |

FOREIGN PATENT DOCUMENTS

| WO | WO 2004/056875 A1 | 7/2004 |
|---|---|---|
| WO | WO 2006/121168 A1 | 11/2006 |
| WO | WO 2008/156712 A1 | 12/2008 |

OTHER PUBLICATIONS

International Search Report related to PCT/EP2014/069170 dated Aug. 12, 2014.
Written Opinion related to PCT/EP2014/069170 dated Aug. 12, 2014.
International Preliminary Report on Patentability related to PCT/EP2014/069170 dated Mar. 15, 2016.

* cited by examiner

*Primary Examiner* — Ilia I Ouspenski

(57) ABSTRACT

The present invention provides antibodies and antigen-binding fragments that specifically bind PD-1 (Programmed Death 1), thereby modulating immune responses in general, and those mediated by TcR and CD28, in particular. The disclosed compositions and methods may be used for example, in treating autoimmune diseases, inflammatory disorders, allergies, transplant rejection, cancer and other immune system disorders.

11 Claims, No Drawings

Specification includes a Sequence Listing.

SEQUENCE LISTING

<160> NUMBER OF SEQ ID NOS: 15

<210> SEQ ID NO 1
<211> LENGTH: 288
<212> TYPE: PRT
<213> ORGANISM: Homo sapiens

<400> SEQUENCE: 1

```
Met Gln Ile Pro Gln Ala Pro Trp Pro Val Val Trp Ala Val Leu Gln
1               5                   10                  15
Leu Gly Trp Arg Pro Gly Trp Phe Leu Asp Ser Pro Asp Arg Pro Trp
            20                  25                  30
Asn Pro Pro Thr Phe Ser Pro Ala Leu Leu Val Val Thr Glu Gly Asp
        35                  40                  45
Asn Ala Thr Phe Thr Cys Ser Phe Ser Asn Thr Ser Glu Ser Phe Val
    50                  55                  60
Leu Asn Trp Tyr Arg Met Ser Pro Ser Asn Gln Thr Asp Lys Leu Ala
65                  70                  75                  80
Ala Phe Pro Glu Asp Arg Ser Gln Pro Gly Gln Asp Cys Arg Phe Arg
                85                  90                  95
Val Thr Gln Leu Pro Asn Gly Arg Asp Phe His Met Ser Val Val Arg
            100                 105                 110
Ala Arg Arg Asn Asp Ser Gly Thr Tyr Leu Cys Gly Ala Ile Ser Leu
        115                 120                 125
Ala Pro Lys Ala Gln Ile Lys Glu Ser Leu Arg Ala Glu Leu Arg Val
    130                 135                 140
Thr Glu Arg Arg Ala Glu Val Pro Thr Ala His Pro Ser Pro Ser Pro
145                 150                 155                 160
Arg Pro Ala Gly Gln Phe Gln Thr Leu Val Val Gly Val Val Gly Gly
                165                 170                 175
Leu Leu Gly Ser Leu Val Leu Leu Val Trp Val Leu Ala Val Ile Cys
            180                 185                 190
Ser Arg Ala Ala Arg Gly Thr Ile Gly Ala Arg Arg Thr Gly Gln Pro
        195                 200                 205
Leu Lys Glu Asp Pro Ser Ala Val Pro Val Phe Ser Val Asp Tyr Gly
    210                 215                 220
Glu Leu Asp Phe Gln Trp Arg Glu Lys Thr Pro Glu Pro Pro Val Pro
225                 230                 235                 240
Cys Val Pro Glu Gln Thr Glu Tyr Ala Thr Ile Val Phe Pro Ser Gly
                245                 250                 255
Met Gly Thr Ser Ser Pro Ala Arg Arg Gly Ser Ala Asp Gly Pro Arg
            260                 265                 270
Ser Ala Gln Pro Leu Arg Pro Glu Asp Gly His Cys Ser Trp Pro Leu
        275                 280                 285

<210> SEQ ID NO 2
<211> LENGTH: 2115
<212> TYPE: DNA
<213> ORGANISM: Homo sapiens

<400> SEQUENCE: 2
agtttccctt ccgctcacct ccgcctgagc agtggagaag gcggcactct ggtgggctg      60 ctccaggcat gcagatccca caggcgccct ggccagtcgt ctgggcggtg ctacaactgg    120
gctggcggcc aggatggttc ttagactccc agacaggcc ctggaacccc ccaccttct     180 ccccagccct gctcgtggtg accgaagggg acaacgccac cttcacctgc agcttctcca    240
acacatcgga gagcttcgtg ctaaactggt accgcatgag cccagcaac cagacggaca    300 agctggccgc cttccccgag gaccgcagcc agcccggcca ggactgccgc ttccgtgtca    360
cacaactgcc caacgggcgt gacttccaca tgagcgtggt cagggcccgg cgcaatgaca    420
gcggcaccta cctctgtggg gccatctccc tggccccccaa ggcgcagatc aaagagagcc    480
```

```
tgcgggcaga gctcagggtg acagagagaa gggcagaagt gcccacagcc caccccagcc    540
cctcacccag gccagccggc cagttccaaa ccctggtggt tggtgtcgtg gcggcctgc    600 tgggcagcct ggtgctgcta gtctgggtcc tggccgtcat ctgctcccgg gccgcacgag    660
ggacaatagg agccaggcgc accggccagc ccctgaagga ggaccctca gccgtgcctg    720 tgttctctgt ggactatggg gagctggatt ccagtggcg agagaagacc ccggagcccc    780
ccgtgccctg tgtccctgag cagacggagt atgccaccat tgtctttcct agcggaatgg    840
gcacctcatc cccgcccgc aggggctcag ctgacggccc tcggagtgcc cagccactga    900
ggcctgagga tggacactgc tcttggcccc tctgaccggc ttccttggcc accagtgttc    960
tgcagaccct ccaccatgag cccgggtcag cgcatttcct caggagaagc aggcagggtg   1020
caggccattg caggccgtcc aggggctgag ctgcctgggg gcgaccgggg ctccagcctg   1080
cacctgcacc aggcacagcc ccaccacagg actcatgtct caatgcccac agtgagccca   1140
ggcagcaggt gtcaccgtcc ctacagggga gggccagatg cagtcactgc ttcaggtcct   1200
gccagcacag agctgcctgc gtccagctcc ctgaatctct gctgctgctg ctgctgctgc   1260
tgctgctgcc tgcggcccgg ggctgaaggc gccgtggccc tgcctgacgc cccggagcct   1320
cctgcctgaa cttgggggct ggttggagat ggccttggag cagccaaggt gcccctggca   1380
gtggcatccc gaaacgccct ggacgcaggg cccaagactg gcacaggag tgggaggtac    1440 atggggctgg gactccca ggagttatct gctcccctgca ggcctagaga gtttcaggg    1500 aaggtcagaa gagctcctgg ctgtggtggg cagggcagga aacccctcca cctttacaca   1560
tgcccaggca gcacctcagg ccctttgtgg ggcaggaag ctgaggcagt aagcgggcag    1620
gcagagctgg aggcctttca ggcccagcca gcactctggc ctcctgccgc cgcattccac   1680 cccagccct cacaccactc gggagaggga catcctacgg tcccaaggtc aggagggcag    1740
ggctggggtt gactcaggcc cctcccagct gtggccacct gggtgttggg agggcagaag   1800
tgcaggcacc tagggccccc catgtgccca ccctgggagc tctccttgga acccattcct   1860
gaaattattt aaaggggttg gccgggctcc caccagggcc tgggtgggaa ggtacaggcg   1920
ttccccgggg gcctagtacc cccgccgtgg cctatccact cctcacatcc acacactgca   1980
cccccactcc tggggcaggg ccaccagcat ccaggcggcc agcaggcacc tgagtggctg   2040
ggacaaggga tccccttcc ctgtggttct attatattat aattataatt aaatatgaga    2100
gcatgctaag gaaaa                                                   2115
```

<210> SEQ ID NO 3
<211> LENGTH: 176
<212> TYPE: PRT
<213> ORGANISM: Homo sapiens

<400> SEQUENCE: 3

```
Met Arg Ile Phe Ala Val Phe Ile Phe Met Thr Tyr Trp His Leu Leu
1               5                   10                  15

Asn Ala Pro Tyr Asn Lys Ile Asn Gln Arg Ile Leu Val Val Asp Pro
            20                  25                  30

Val Thr Ser Glu His Glu Leu Thr Cys Gln Ala Glu Gly Tyr Pro Lys
        35                  40                  45

Ala Glu Val Ile Trp Thr Ser Ser Asp His Gln Val Leu Ser Gly Lys
    50                  55                  60

Thr Thr Thr Thr Asn Ser Lys Arg Glu Glu Lys Leu Phe Asn Val Thr
65                  70                  75                  80
```

```
Ser Thr Leu Arg Ile Asn Thr Thr Asn Glu Ile Phe Tyr Cys Thr
                85                  90                  95

Phe Arg Arg Leu Asp Pro Glu Glu Asn His Thr Ala Glu Leu Val Ile
            100                 105                 110

Pro Glu Leu Pro Leu Ala His Pro Pro Asn Glu Arg Thr His Leu Val
        115                 120                 125

Ile Leu Gly Ala Ile Leu Leu Cys Leu Gly Val Ala Leu Thr Phe Ile
130                 135                 140

Phe Arg Leu Arg Lys Gly Arg Met Met Asp Val Lys Lys Cys Gly Ile
145                 150                 155                 160

Gln Asp Thr Asn Ser Lys Lys Gln Ser Asp Thr His Leu Glu Glu Thr
                165                 170                 175

<210> SEQ ID NO 4
<211> LENGTH: 3349
<212> TYPE: DNA
<213> ORGANISM: Homo sapiens

<400> SEQUENCE: 4
```

| | | | | | |
|---|---|---|---|---|---|
| ggcgcaacgc | tgagcagctg | gcgcgtcccg | cgcggcccca | gttctgcgca | gcttcccgag | 60 |
| gctccgcacc | agccgcgctt | ctgtccgcct | gcagggcatt | ccagaaagat | gaggatattt | 120 |
| gctgtcttta | tattcatgac | ctactggcat | ttgctgaacg | ccccatacaa | caaaatcaac | 180 |
| caaagaattt | tggttgtgga | tccagtcacc | tctgaacatg | aactgacatg | tcaggctgag | 240 |
| ggctacccca | aggccgaagt | catctggaca | agcagtgacc | atcaagtcct | gagtggtaag | 300 |
| accaccacca | ccaattccaa | gagagaggag | aagcttttca | atgtgaccag | cacactgaga | 360 |
| atcaacacaa | caactaatga | gatttttctac | tgcactttta | ggagattaga | tcctgaggaa | 420 |
| aaccatacag | ctgaattggt | catcccagaa | ctacctctgg | cacatcctcc | aaatgaaagg | 480 |
| actcacttgg | taattctggg | agccatctta | ttatgccttg | gtgtagcact | gacattcatc | 540 |
| ttccgtttaa | gaaagggag | aatgatggat | gtgaaaaaat | gtggcatcca | agatacaaac | 600 |
| tcaaagaagc | aaagtgatac | acatttggag | gagacgtaat | ccagcattgg | aacttctgat | 660 |
| cttcaagcag | ggattctcaa | cctgtggttt | aggggttcat | cggggctgag | cgtgacaaga | 720 |
| ggaaggaatg | ggcccgtggg | atgcaggcaa | tgtgggactt | aaaaggccca | agcactgaaa | 780 |
| atggaacctg | gcgaaagcag | aggaggagaa | tgaagaaaga | tggagtcaaa | cagggagcct | 840 |
| ggagggagac | cttgatactt | tcaaatgcct | gaggggctca | tcgacgcctg | tgacagggag | 900 |
| aaaggatact | tctgaacaag | gagcctccaa | gcaaatcatc | cattgctcat | cctaggaaga | 960 |
| cgggttgaga | atccctaatt | tgagggtcag | ttcctgcaga | agtgcccttt | gcctccactc | 1020 |
| aatgcctcaa | tttgttttct | gcatgactga | gagtctcagt | gttggaacgg | gacagtattt | 1080 |
| atgtatgagt | ttttcctatt | tattttgagt | ctgtgaggtc | ttcttgtcat | gtgagtgtgg | 1140 |
| ttgtgaatga | tttcttttga | agatatattg | tagtagatgt | tacaattttg | tcgccaaact | 1200 |
| aaacttgctg | cttaatgatt | tgctcacatc | tagtaaaaca | tggagtattt | gtaaggtgct | 1260 |
| tggtctcctc | tataactaca | agtatacatt | ggaagcataa | agatcaaacc | gttggttgca | 1320 |
| taggatgtca | cctttattta | acccattaat | actctggttg | acctaatctt | attctcagac | 1380 |
| ctcaagtgtc | tgtgcagtat | ctgttccatt | taaatatcag | ctttacaatt | atgtggtagc | 1440 |
| ctacacacat | aatctcattt | catcgctgta | accaccctgt | tgtgataacc | actattattt | 1500 |
| tacccatcgt | acagctgagg | aagcaaacag | attaagtaac | ttgcccaaac | cagtaaatag | 1560 |
| cagacctcag | actgccaccc | actgtccttt | tataatacaa | tttacagcta | tatttactt | 1620 |

```
taagcaattc ttttattcaa aaaccattta ttaagtgccc ttgcaatatc aatcgctgtg      1680
ccaggcattg aatctacaga tgtgagcaag acaaagtacc tgtcctcaag gagctcatag      1740
tataatgagg agattaacaa gaaaatgtat tattacaatt tagtccagtg tcatagcata      1800
aggatgatgc gaggggaaaa cccgagcagt gttgccaaga ggaggaaata ggccaatgtg      1860
gtctgggacg gttggatata cttaaacatc ttaataatca gagtaatttt catttacaaa      1920
gagaggtcgg tacttaaaat aaccctgaaa ataacactg gaattccttt tctagcatta      1980
tatttattcc tgatttgcct ttgccatata atctaatgct tgtttatata gtgtctggta      2040
ttgtttaaca gttctgtctt ttctatttaa atgccactaa attttaaatt catacctttc      2100
catgattcaa aattcaaaag atcccatggg agatggttgg aaaatctcca cttcatcctc      2160
caagccattc aagtttcctt tccagaagca actgctactg cctttcattc atatgttctt      2220
ctaaagatag tctacatttg gaaatgtatg ttaaaagcac gtattttaaa aatttttttc      2280
ctaaatagta acacattgta tgtctgctgt gtactttgct attttatttt attttagtgt      2340
ttcttatata gcagatggaa tgaatttgaa gttcccaggg ctgaggatcc atgccttctt      2400
tgtttctaag ttatctttcc catagctttt cattatcttt catatgatcc agtatatgtt      2460
aaatatgtcc tacatataca tttagacaac caccatttgt taagtatttg ctctaggaca      2520
gagtttggat ttgtttatgt ttgctcaaaa ggagacccat gggctctcca gggtgcactg      2580
agtcaatcta gtcctaaaaa gcaatcttat tattaactct gtatgacaga atcatgtctg      2640
gaacttttgt tttctgcttt ctgtcaagta taaacttcac tttgatgctg tacttgcaaa      2700
atcacatttt ctttctggaa attccggcag tgtaccttga ctgctagcta ccctgtgcca      2760
gaaaagcctc attcgttgtg cttgaaccct tgaatgccac cagctgtcat cactacacag      2820
ccctcctaag aggcttcctg gaggtttcga gattcagatg ccctgggaga tcccagagtt      2880
tcctttccct cttggccata ttctggtgtc aatgacaagg agtaccttgg ctttgccaca      2940
tgtcaaggct gaagaaacag tgtctccaac agagctcctt gtgttatctg tttgtacatg      3000
tgcatttgta cagtaattgg tgtgacagtg ttctttgtgt gaattacagg caagaattgt      3060
ggctgagcaa ggcacatagt ctactcagtc tattcctaag tcctaactcc tccttgtggt      3120
gttggatttg taaggcactt tatccctttt gtctcatgtt tcatcgtaaa tggcataggc      3180
agagatgata cctaattctg catttgattg tcactttttg tacctgcatt aatttaataa      3240
aatattctta tttattttgt tacttggtac accagcatgt ccattttctt gtttattttg      3300
tgtttaataa aatgttcagt ttaacatccc agtggagaaa gttaaaaaa              3349
```

<210> SEQ ID NO 5
<211> LENGTH: 273
<212> TYPE: PRT
<213> ORGANISM: Homo sapiens

<400> SEQUENCE: 5

```
Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60
```

```
Asp Thr Ser Pro His Arg Glu Arg Ala Thr Leu Leu Glu Glu Gln Leu
 65                  70                  75                  80

Pro Leu Gly Lys Ala Ser Phe His Ile Pro Gln Val Gln Val Arg Asp
                 85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
    210                 215                 220

Ile Phe Ile Pro Phe Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala
                260                 265                 270

Ile

<210> SEQ ID NO 6
<211> LENGTH: 2418
<212> TYPE: DNA
<213> ORGANISM: Homo sapiens

<400> SEQUENCE: 6
gcaaacctta agctgaatga acaacttttc ttctcttgaa tatatcttaa cgccaaattt      60
tgagtgcttt tttgttaccc atcctcatat gtcccagcta gaaagaatcc tgggttggag     120
ctactgcatg ttgattgttt tgttttttcct tttggctgtt catttggtg gctactataa     180 ggaaatctaa cacaaacagc aactgttttt tgttgtttac ttttgcatct ttacttgtgg     240
agctgtggca gtcctcata tcaaatacag aacatgatct tcctcctgct aatgttgagc      300
ctggaattgc agcttcacca gatagcagct ttattcacag tgacagtccc taaggaactg     360
tacataatag agcatggcag caatgtgacc ctggaatgca actttgacac tggaagtcat     420 gtgaacttg gagcaataac agccagtttg caaaaggtgg aaaatgatac atccccacac     480
cgtgaaagag ccactttgct ggaggagcag ctgccctag ggaaggcctc gttccacata    540
cctcaagtcc aagtgaggga cgaaggacag taccaatgca taatcatcta tggggtcgcc    600
tgggactaca gtacctgac tctgaaagtc aaagcttcct acaggaaaat aaacactcac    660
atcctaaagg ttccagaaac agatgaggta gagctcacct gccaggctac aggttatcct    720
ctggcagaag tatcctggcc aaacgtcagc gttcctgcca acaccagcca ctccaggacc   780
cctgaaggcc tctaccaggt caccagtgtt ctgcgcctaa agccaccccc tggcagaaac    840
ttcagctgtg tgttctggaa tactcacgtg agggaactta ctttggccag cattgacctt    900
```

```
caaagtcaga tggaacccag gacccatcca acttggctgc ttcacatttt catcccttc      960
tgcatcattg ctttcatttt catagccaca gtgatagccc taagaaaaca actctgtcaa    1020
aagctgtatt cttcaaaaga cacaacaaaa agacctgtca ccacaacaaa gagggaagtg    1080
aacagtgcta tctgaacctg tggtcttggg agccagggtg acctgatatg acatctaaag    1140
aagcttctgg actctgaaca agaattcggt ggcctgcaga gcttgccatt tgcacttttc    1200
aaatgccttt ggatgaccca gcactttaat ctgaaacctg caacaagact agccaacacc    1260
tggccatgaa acttgcccct tcactgatct ggactcacct ctggagccta tggctttaag    1320
caagcactac tgcactttac agaattaccc cactggatcc tggacccaca gaattccttc    1380
aggatccttc ttgctgccag actgaaagca aaggaatta tttcccctca gttttctaa    1440
gtgatttcca aaagcagagg tgtgtggaaa tttccagtaa cagaaacaga tgggttgcca    1500
atagagttat ttttatcta tagcttcctc tgggtactag aagaggctat tgagactatg    1560
agctcacaga cagggcttcg cacaaactca aatcataatt gacatgtttt atggattact    1620
ggaatcttga tagcataatg aagttgttct aattaacaga gagcatttaa atatacacta    1680
agtgcacaaa ttgtggagta aagtcatcaa gctctgtttt tgaggtctaa gtcacaaagc    1740
atttgtttta acctgtaatg gcaccatgtt taatggtggt ttttttttg aactacatct     1800
ttccttttaaa aattattggt ttcttttttat ttgtttttac cttagaaatc aattatatac   1860
agtcaaaaat atttgtatatg ctcatacgtt gtatctgcag caatttcaga taagtagcta   1920
aaatggccaa agccccaaac taagcctcct tttctggccc tcaatatgac tttaaatttg   1980
actttttcagt gcctcagttt gcacatctgt aatacagcaa tgctaagtag tcaaggcctt  2040
tgataattgg cactatggaa atcctgcaag atcccactac atatgtgtgg agcagaaggg   2100
taactcggct acagtaacag cttaattttg ttaaattttgt tctttatact ggagccatga   2160
agctcagagc attagctgac ccttgaacta ttcaaatggg cacattagct agtataacag   2220
acttacatag gtgggcctaa agcaagctcc ttaactgagc aaaatttggg gcttatgaga   2280
atgaaagggt gtgaaattga ctaacagaca aatcatacat ctcagtttct caattctcat   2340
gtaaatcaga gaatgccttt aaagaataaa actcaattgt tattcttcaa cgttctttat   2400
atattctact tttgggta                                                  2418
```

<210> SEQ ID NO 7
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Ala Tyr Tyr Trp Ser Trp Ile Arg Gln His Pro Gly Lys Gly Leu Glu
        35                  40                  45

Trp Ile Gly Tyr Ile Tyr Tyr Asn Gly Asn Thr Tyr Tyr Asn Pro Ser
    50                  55                  60

Leu Arg Ser Arg Val Thr Ile Ser Val Asp Thr Ser Lys Asn Gln Phe
65                  70                  75                  80
```

```
Ser Leu Lys Leu Ser Ser Val Thr Ala Ala Asp Thr Ala Val Tyr Tyr
            85                  90                  95

Cys Val Arg Ala Ser Asp Tyr Val Trp Gly Tyr His Tyr Phe Asp
            100                 105                 110

Ala Phe Asp Leu Trp Gly Arg Gly Thr Leu Val Thr Val Ser Ser
        115                 120                 125

<210> SEQ ID NO 8
<211> LENGTH: 381
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 8
caggtgcagc tgcaggagtc gggcccagga ctggtgaagc cttcacagac cctgtccctc    60
acctgcactg tctctggtgg ctccatcagc agtggtgctt attactggag ctggatccgc   120
cagcacccag ggaagggcct ggagtggatt ggtacatct attacaatgg aaacacgtac    180
tacaacccgt ccctcaggag tcgagttacc atatcagtag acacgtctaa gaaccagttc   240
tccctgaagc tgagctctgt gactgccgcg gacacggccg tctattactg tgtgagagcg   300
tctgattacg tttggggggg ttatcattat ttcgacgcgt tcgacctctg gggccgggga   360
accctggtca ccgtctcctc a                                              381

<210> SEQ ID NO 9
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Gln Ser Val Leu Thr Gln Pro Pro Ser Ala Ser Gly Thr Pro Gly Gln
1               5                   10                  15

Arg Val Thr Ile Ser Cys Ser Gly Ser Asn Ser Asn Ile Gly Ser Asn
            20                  25                  30

Ser Val Asn Trp Tyr Gln Gln Leu Pro Gly Thr Ala Pro Lys Leu Leu
        35                  40                  45

Ile Tyr Gly Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Val Thr Val Leu
            100                 105                 110

<210> SEQ ID NO 10
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 10
```

```
cagtctgtgc tgactcagcc accctcagcg tctgggaccc ccgggcagag ggtcaccatc    60
tcttgttctg gaagcaactc caacatcgga agtaattctg taaactggta ccagcagctc   120
ccaggaacgg cccccaaact cctcatctat ggtaataatc agcggccctc agggtccct    180 gaccgattct ctggctccaa gtctggcacc tcagcctccc tggccatcag tgggctccag   240
tctgaggatg aggctgatta ttactgtgca gcatgggatg acagcctgaa tggtccggta   300
ttcggcggag ggaccaaggt caccgtccta                                    330
```

<210> SEQ ID NO 11
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: MOD_RES
<222> LOCATION: (1)..(1)
<223> OTHER INFORMATION: Pyroglutamic acid

<400> SEQUENCE: 11

```
Xaa Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Ala Tyr Tyr Trp Ser Trp Ile Arg Gln His Pro Gly Lys Gly Leu Glu
        35                  40                  45

Trp Ile Gly Tyr Ile Tyr Tyr Asn Gly Asn Thr Tyr Tyr Asn Pro Ser
    50                  55                  60

Leu Arg Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Val Arg Ala Ser Asp Tyr Val Trp Gly Gly Tyr His Tyr Phe Asp
            100                 105                 110

Ala Phe Asp Leu Trp Gly Arg Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Phe Glu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270
```

Val Val Asp Val Ser His Glu Asp Pro Glu Val Lys Phe Asn Trp Tyr
            275                 280                 285

Val Asp Gly Val Glu Val His Asn Ala Lys Thr Lys Pro Arg Glu Glu
        290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
            325                 330                 335

Ala Leu Pro Ala Ser Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
            435                 440                 445

Lys Ser Leu Ser Leu Ser Pro Gly
            450                 455

<210> SEQ ID NO 12
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Pyroglutamic acid

<400> SEQUENCE: 12

Xaa Ser Val Leu Thr Gln Pro Pro Ser Ala Ser Gly Thr Pro Gly Gln
1               5                   10                  15

Arg Val Thr Ile Ser Cys Ser Gly Ser Asn Ser Asn Ile Gly Ser Asn
            20                  25                  30

Ser Val Asn Trp Tyr Gln Gln Leu Pro Gly Thr Ala Pro Lys Leu Leu
        35                  40                  45

Ile Tyr Gly Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Val Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

```
Pro Gly Ala Val Thr Val Ala Trp Lys Ala Asp Ser Ser Pro Val Lys
145                 150                 155                 160

Ala Gly Val Glu Thr Thr Pro Ser Lys Gln Ser Asn Asn Lys Tyr
                165             170                 175

Ala Ala Ser Ser Tyr Leu Ser Leu Thr Pro Glu Gln Trp Lys Ser His
            180             185                 190

Arg Ser Tyr Ser Cys Gln Val Thr His Glu Gly Ser Thr Val Glu Lys
        195             200                 205

Thr Val Ala Pro Thr Glu Cys Ser
    210             215

<210> SEQ ID NO 13
<211> LENGTH: 6
<212> TYPE: PRT
<213> ORGANISM: Mus sp.

<400> SEQUENCE: 13

Val Ala Tyr Glu Glu Leu
1               5

<210> SEQ ID NO 14
<211> LENGTH: 6
<212> TYPE: PRT
<213> ORGANISM: Unknown
<220> FEATURE:
<221> NAME/KEY: source
<223> OTHER INFORMATION: /note="Description of Unknown:
      ITIM-like motif derived from human or mouse"

<400> SEQUENCE: 14

Thr Glu Tyr Ala Thr Ile
1               5

<210> SEQ ID NO 15
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gly Gly Gly Gly Ser Gly Gly Gly Gly Ser Gly Gly Gly Gly Ser
1               5                   10                  15
```

ANTIBODIES AGAINST PD-1 AND USES THEREOF

CROSS-REFERENCE TO RELATED APPLICATIONS

This application is a U.S. National Stage application of International Application No. PCT/EP2014/069170, filed on Sep. 9, 2014, said International Application No. PCT/EP2014/069170 claims benefit under 35 U.S.C. § 119(e) of the U.S. Provisional Application No. 61/875,847, filed Sep. 10, 2013. Each of the above listed applications is incorporated by reference herein in its entirety for all purposes.

REFERENCE TO THE SEQUENCE LISTING

This application incorporates by reference a Sequence Listing submitted with this application as text file entitled PD1-101US1_SEQ, created on Mar. 9, 2016, and having a size of 27.2 kilobytes.

BACKGROUND OF THE INVENTION

An adaptive immune response involves activation, selection, and clonal proliferation of two major classes of lymphocytes termed T cells and B cells. After encountering an antigen, T cells proliferate and differentiate into antigen-specific effector cells, while B cells proliferate and differentiate into antibody-secreting cells.

T cell activation is a multi-step process requiring several signaling events between the T cell and an antigen-presenting cell (APC). For T cell activation to occur, two types of signals must be delivered to a resting T cell. The first type is mediated by the antigen-specific T cell receptor (TcR), and confers specificity to the immune response. The second, costimulatory, type regulates the magnitude of the response and is delivered through accessory receptors on the T cell.

A primary costimulatory signal is delivered through the activating CD28 receptor upon engagement of its ligands B7-1 or B7-2. In contrast, engagement of the inhibitory CTLA-4 receptor by the same B7-1 or B7-2 ligands results in attenuation of T cell response. Thus, CTLA-4 signals antagonize costimulation mediated by CD28. At high antigen concentrations, CD28 costimulation overrides the CTLA-4 inhibitory effect. Temporal regulation of the CD28 and CTLA-4 expression maintains a balance between activating and inhibitory signals and ensures the development of an effective immune response, while safeguarding against the development of autoimmunity.

Molecular homologues of CD28 and CTLA-4 and their B-7 like ligands have been recently identified. ICOS is a CD28-like costimulatory receptor. PD-1 (Programmed Death 1) is an inhibitory receptor and a counterpart of CTLA-4. In one example, binding of PD-L1 with its receptor PD-1 on T cells delivers a signal that inhibits TCR-mediated activation of IL-2 production and T cell proliferation. This disclosure relates to modulation of immune responses mediated by the PD-1 receptor.

PD-1 is a 50-55 kDa type I transmembrane receptor that was originally identified in a T cell line undergoing activation-induced apoptosis. PD-1 is expressed on T cells, B cells, and macrophages. The ligands for PD-1 are the B7 family members PD-L1 (B7-H1) and PD-L2 (B7-DC).

PD-1 is a member of the immunoglobulin (Ig) superfamily that contains a single Ig V-like domain in its extracellular region. The PD-1 cytoplasmic domain contains two tyrosines, with the most membrane-proximal tyrosine (VAYEEL in mouse PD-1) located within an ITIM (immuno-receptor tyrosine-based inhibitory motif). The presence of an ITIM on PD-1 indicates that this molecule functions to attenuate antigen receptor signaling by recruitment of cytoplasmic phosphatases. Human and murine PD-1 proteins share about 60% amino acid identity with conservation of four potential N-glycosylation sites, and residues that define the Ig-V domain. The ITIM in the cytoplasmic region and the ITIM-like motif surrounding the carboxy-terminal tyrosine (TEYATI in human and mouse) are also conserved between human and murine orthologues.

PD-1 is expressed on activated T cells, B cells, and monocytes. Experimental data implicates the interactions of PD-1 with its ligands in downregulation of central and peripheral immune responses. In particular, proliferation in wild-type T cells but not in PD-1-deficient T cells is inhibited in the presence of PD-L1. Additionally, PD-1-deficient mice exhibit an autoimmune phenotype. PD-1 deficiency in the C57BL/6 mice results in chronic progressive lupus-like glomerulonephritis and arthritis. In Balb/c mice, PD-1 deficiency leads to severe cardiomyopathy due to the presence of heart-tissue-specific self-reacting antibodies.

In general, a need exists to provide safe and effective therapies for immune disorders such as, for example, autoimmune diseases, inflammatory disorders, allergies, transplant rejection, cancer, immune deficiency, and other immune system-related disorders. Modulation of the immune responses involved in these disorders can be accomplished by manipulation of the PD-1 pathway.

SUMMARY OF THE INVENTION

As described below, the present invention features antibodies that can act as antagonists of PD-1, thereby modulating immune responses regulated by PD-1. The disclosure further provides anti-PD-1 antibodies that comprise novel antigen-binding fragments.

In certain embodiments, an isolated antibody or antigen-binding fragment thereof of the invention specifically binds to a PD-1 polypeptide and comprises a VH and/or a VL domain, where the VH and/or VL domain are each identical to or each have at least 90%, 95%, or 98% identity to the VH and VL amino acid sequences of SEQ ID NOs: 7 and 9. In particular embodiments, the isolated antibody or antigen-binding fragment thereof comprises a $V_H$ domain of LOPD180 corresponding to SEQ ID NO: 7 and/or a $V_L$ domain of LOPD180 corresponding to SEQ ID NO: 9.

In further embodiments, the isolated antibody or antigen-binding fragment thereof comprises a $V_H$ domain or an antigen-binding fragment thereof that comprises 3 CDRs of LOPD180; and a $V_L$ domain or an antigen-binding fragment thereof that comprises 3 CDRs of LOPD180. In other embodiments, the isolated antibody or antigen-binding fragment thereof that consists essentially of LOPD180.

In additional embodiments, the isolated antibody or antigen-binding fragment thereof specifically binds an epitope within the extracellular domain of human or mouse PD-1. In other embodiments, the isolated antibody or antigen-binding fragment thereof is an antigen binding fragment Fab, F(ab')$_2$, Fv, scFv, Fd or dAb.

In certain embodiments, the isolated antibody or antigen-binding fragment thereof specifically binds to the extracellular domain of PD-1 with an affinity constant greater than $10^7$ M$^{-1}$. In other embodiments, the isolated antibody or antigen-binding fragment thereof inhibits the binding of PD-L1 or PD-L2 to PD-1 with an IC$_{50}$ of less than 10 nM.

In further embodiments, the isolated antibody or antigen-binding fragment thereof is a human antibody or antigen-binding fragment thereof. In other embodiments the antibody is an $IgG_1$ or $IgG_4$. In further embodiments, the antibody is an $IgG_{1\lambda}$ or $IgG_{1\kappa}$.

In particular embodiments, the isolated antibody or antigen-binding fragment thereof of comprises a VH and/or a VL domain where the VH domain comprises H1, H2 and H3 regions, where H1 corresponds to amino acids 31-37 of SEQ ID NO: 7, where H2 corresponds to amino acids 52-67 of SEQ ID NO: 7, and where H3 corresponds to amino acids 110-116 of SEQ ID NO: 7 and/or the VL domain comprises L1, L2 and L3 regions, where L1 corresponds to amino acids 23-35 of SEQ ID NO: 9, where L2 corresponds to amino acids 51-57 of SEQ ID NO: 9, and where L3 corresponds to amino acids 90-100 of SEQ ID NO: 9.

The invention further provides for a pharmaceutical composition comprising the isolated antibody or antigen-binding fragment thereof of the invention The invention also provides for a kit comprising the isolated antibody or antigen-binding fragment thereof of the invention, and directions for the use of the antibody in an immunological assay.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "PD-1 polypeptide" is meant a polypeptide or fragment thereof having at least about 85% amino acid identity to NCBI Accession No. NP_005009 and having PD-L1 and/or PD-L2 binding activity.

By "PD-1 nucleic acid molecule" is meant a polynucleotide encoding a PD-1 polypeptide. An exemplary PD-1 nucleic acid molecule sequence is provided at NCBI Accession No. NM_005018.

By "PD-L1 polypeptide" is meant a polypeptide or fragment thereof having at least about 85% amino acid identity to NCBI Accession No. NP_001254635 and having PD-1 binding activity.

By "PD-L1 nucleic acid molecule" is meant a polynucleotide encoding a PD-L1 polypeptide. An exemplary PD-L1 nucleic acid molecule sequence is provided at NCBI Accession No. NM_001267706.

By "PD-L2 polypeptide" is meant a polypeptide or fragment thereof having at least about 85% amino acid identity to NCBI Accession No. NP_079515 and having PD-1 binding activity.

By "PD-L2 nucleic acid molecule" is meant a polynucleotide encoding a PD-L2 polypeptide. An exemplary PD-L2 nucleic acid molecule sequence is provided at NCBI Accession No. NM_025239.

Select exemplary sequences delineated herein are described below.

A "biomarker" or "marker" as used herein generally refers to a protein, nucleic acid molecule, clinical indicator, or other analyte that is associated with a disease. In one embodiment, a marker of a disease is differentially present in a biological sample obtained from a subject having or at risk of developing the disease relative to a reference. A marker is differentially present if the mean or median level of the biomarker present in the sample is statistically different from the level present in a reference. A reference level may be, for example, the level present in a sample obtained from a healthy control subject or the level obtained from the subject at an earlier timepoint, i.e., prior to treatment. Common tests for statistical significance include, among others, t-test, ANOVA, Kruskal-Wallis, Wilcoxon, Mann-Whitney and odds ratio. Biomarkers, alone or in combination, provide measures of relative likelihood that a subject belongs to a phenotypic status of interest. The differential presence of a marker of the invention in a subject sample can be useful in characterizing the subject as having or at risk of developing an immune disorder, for determining the prognosis of the subject, for evaluating therapeutic efficacy, or for selecting a treatment regimen.

"Biological activity" when used herein in the context of a PD-1 or PD-L1 polypeptide refers to a biological function that results from the activity of the native PD-1 and/or PD-L1 polypeptide. A particular PD-1 and/or PD-L1 biological activity includes, for example, negative regulation of immune responses, reduced T cell proliferation, and reduced IFN-γ production, and/or reduced IL-2 production.

By "agent" is meant any small molecule chemical compound, antibody, nucleic acid molecule, or polypeptide, or fragments thereof.

By "alteration" or "change" is meant an increase or decrease. An alteration may be by as little as 1%, 2%, 3%, 4%, 5%, 10%, 20%, 30%, or by 40%, 50%, 60%, or even by as much as 70%, 75%, 80%, 90%, or 100%.

The term "antibody," as used in this disclosure, refers to an immunoglobulin or a fragment or a derivative thereof, and encompasses any polypeptide comprising an antigen-binding site, regardless whether it is produced in vitro or in vivo. The term includes, but is not limited to, polyclonal, monoclonal, monospecific, polyspecific, non-specific, humanized, single-chain, chimeric, synthetic, recombinant, hybrid, mutated, and grafted antibodies. Unless otherwise modified by the term "intact," as in "intact antibodies," for the purposes of this disclosure, the term "antibody" also includes antibody fragments such as Fab, F(ab')$_2$, Fv, scFv, Fd, dAb, and other antibody fragments that retain antigen-binding function, i.e., the ability to bind PD-1 specifically. Typically, such fragments would comprise an antigen-binding domain.

The terms "antigen-binding domain," "antigen-binding fragment," and "binding fragment" refer to a part of an antibody molecule that comprises amino acids responsible for the specific binding between the antibody and the antigen. In instances, where an antigen is large, the antigen-binding domain may only bind to a part of the antigen. A portion of the antigen molecule that is responsible for specific interactions with the antigen-binding domain is referred to as "epitope" or "antigenic determinant" An antigen-binding domain typically comprises an antibody light chain variable region ($V_L$) and an antibody heavy chain variable region ($V_H$), however, it does not necessarily have to comprise both. For example, a so-called Fd antibody fragment consists only of a $V_H$ domain, but still retains some antigen-binding function of the intact antibody.

Binding fragments of an antibody are produced by recombinant DNA techniques, or by enzymatic or chemical cleavage of intact antibodies. Binding fragments include Fab, Fab', F(ab')2, Fv, and single-chain antibodies. An antibody other than a "bispecific" or "bifunctional" antibody is understood to have each of its binding sites identical. Digestion of antibodies with the enzyme, papain, results in two identical antigen-binding fragments, known also as "Fab" fragments, and a "Fc" fragment, having no antigen-binding activity but having the ability to crystallize. Digestion of antibodies with the enzyme, pepsin, results in the a F(ab')2 fragment in which the two arms of the antibody molecule remain linked and comprise two-antigen binding sites. The F(ab')2 fragment has the ability to crosslink antigen. "Fv" when used herein refers to the minimum fragment of an antibody that retains both antigen-recognition and antigen-binding sites. "Fab" when used herein refers to a fragment of an antibody that comprises the constant domain of the light chain and the CHI domain of the heavy chain.

The term "mAb" refers to monoclonal antibody. Antibodies of the invention comprise without limitation whole native antibodies, bispecific antibodies; chimeric antibodies; Fab, Fab', single chain V region fragments (scFv), fusion polypeptides, and unconventional antibodies.

By "biologic sample" is meant any tissue, cell, fluid, or other material derived from an organism.

By "capture reagent" is meant a reagent that specifically binds a nucleic acid molecule or polypeptide to select or isolate the nucleic acid molecule or polypeptide.

As used herein, the terms "determining", "assessing", "assaying", "measuring" and "detecting" refer to both quantitative and qualitative determinations, and as such, the term "determining" is used interchangeably herein with "assaying," "measuring," and the like. Where a quantitative determination is intended, the phrase "determining an amount" of an analyte and the like is used. Where a qualitative and/or quantitative determination is intended, the phrase "determining a level" of an analyte or "detecting" an analyte is used.

The term "effective amount" refers to a dosage or amount that is sufficient to reduce the activity of PD-1 to result in amelioration of symptoms in a patient or to achieve a desired biological outcome. Desired biological outcomes include, for example, increased cytolytic activity of T cells, induction of immune tolerance, reduction or increase of the PD-1 activity associated with the negative regulation of T-cell mediated immune response.

The term "isolated" refers to a molecule that is substantially free of other elements present in its natural environment. For instance, an isolated protein is substantially free of cellular material or other proteins from the cell or tissue source from which it is derived. The term "isolated" also refers to preparations where the isolated protein is sufficiently pure to be administered as a pharmaceutical composition, or at least 70-80% (w/w) pure, more preferably, at least 80-90% (w/w) pure, even more preferably, 90-95% pure; and, most preferably, at least 95%, 96%, 97%, 98%, 99%, or 100% (w/w) pure.

The term "subject" or "patient" refers to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

The term "reduce" or "increase" is meant to alter negatively or positively, respectively. An alteration may be by 5%, 10%, 25%, 30%, 50%, 75%, or even by 100%.

By "reference" is meant a standard of comparison. For example, when describing the level of sequence identity of a polypeptide or nucleic acid molecule, the level of sequence identity may be expressed as a percentage of the amino acid or nucleotides in common with a reference sequence when the sequence of the polypeptide or nucleic acid molecule aligned with a reference sequence. In another example, the PD-1 or PD-L1 polypeptide or polynucleotide level present in a patient sample may be compared to the level of said polypeptide or polynucleotide present in a corresponding healthy cell or tissue. In one embodiment, the standard of comparison is the level of PD-1 or PD-L1 polypeptide or polynucleotide level present in serum of a subject that does not have an immune disorder.

The term "repertoire" refers to a genetically diverse collection of nucleotides derived wholly or partially from sequences that encode expressed immunoglobulins. The sequences are generated by in vivo rearrangement of, e.g., V, D, and J segments for H chains and, e.g., V and J segment for L chains. Alternatively, the sequences may be generated from a cell line by in vitro stimulation, in response to which the rearrangement occurs. Alternatively, part or all of the sequences may be obtained by combining, e.g., unrearranged V segments with D and J segments, by nucleotide synthesis, randomised mutagenesis, and other methods, e.g., as disclosed in U.S. Pat. No. 5,565,332.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95%, 96%, 97%, 98%, or even 99% or more identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

As used herein, the term "sample" includes a biologic sample such as any tissue, cell, fluid, or other material derived from an organism.

By "specifically binds" is meant a compound (e.g., antibody) that recognizes and binds a molecule (e.g., polypeptide), but which does not substantially recognize and bind other molecules in a sample, for example, a biological sample. For example, two molecules that specifically bind form a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the affinity constant $K_A$ is higher than $10^6 M^{-1}$, or more preferably higher than $10^8 M^{-1}$. If necessary, non-specific binding can be reduced without substantially affecting specific binding by varying the binding conditions. The appropriate binding conditions such as concentration of antibodies, ionic strength of the solution, temperature, time allowed for binding, concentration of a blocking agent (e.g., serum albumin, milk casein), etc., may be optimized by a skilled artisan using routine techniques.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Any compounds, compositions, or methods provided herein can be combined with one or more of any of the other compositions and methods provided herein.

As used herein, the singular forms "a", "an", and "the" include plural forms unless the context clearly dictates otherwise. Thus, for example, reference to "a biomarker" includes reference to more than one biomarker.

Unless specifically stated or obvious from context, as used herein, the term "or" is understood to be inclusive.

The term "including" is used herein to mean, and is used interchangeably with, the phrase "including but not limited to."

As used herein, the terms "comprises," "comprising," "containing," "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

DETAILED DESCRIPTION OF THE INVENTION

The invention features antibodies that can act as antagonists of PD-1 or a PD-1 pathway, thereby modulating immune responses regulated by PD-1. The disclosure further provides anti-PD-1 antibodies that comprise novel antigen-binding fragments. Anti-PD-1 antibodies of the invention are capable of (a) specifically binding to PD-1, including human PD-1; (b) blocking PD-1 interactions with its natural ligand(s) (e.g., PD-L1, PD-L2); or (c) performing both functions. Furthermore, the antibodies possess immunomodulatory properties, i.e., they are effective in modulating PD-1-associated immune responses. Depending on the method of use and the desired effect, the antibodies may be used to either enhance or inhibit immune responses.

A nonlimiting, illustrative embodiment of the antibodies of the invention is referred to herein as LOPD180. Other embodiments comprise a $V_H$ and/or $V_L$ domain of the Fv fragment of LOPD180. Further embodiments comprise one or more complementarity determining regions (CDRs) of any of these $V_H$ and $V_L$ domains. Other embodiments comprise an H3 fragment of the $V_H$ domain of LOPD180.

The disclosure also provides compositions comprising anti-PD-1 antibodies, and their use in methods of modulating immune response, including methods of treating humans or animals. In particular embodiments, anti-PD-1 antibodies are used to treat or prevent immune disorders by virtue of increasing or reducing the T cell response mediated by TcR/CD28. Disorders susceptible to treatment with compositions of the invention include but are not limited to rheumatoid arthritis, multiple sclerosis, inflammatory bowel disease, Crohn's disease, systemic lupus erythematosis, type I diabetes, transplant rejection, graft-versus-host disease, hyperproliferative immune disorders, cancer, and infectious diseases.

Additionally, anti-PD-1 antibodies may be used diagnostically to detect PD-1 or its fragments in a biological sample. The amount of PD-1 detected may be correlated with the expression level of PD-1, which, in turn, is correlated with the activation status of immune cells (e.g., activated T cells, B cells, and monocytes) in the subject.

The disclosure also provides isolated nucleic acids, which comprise a sequence encoding a $V_H$ or $V_L$ domain from the Fv fragment of LOPD180. Also provided are isolated nucleic acids, which comprise a sequence encoding one or more CDRs from any of the presently disclosed $V_H$ and $V_L$ domains. The disclosure also provides vectors and host cells comprising such nucleic acids.

The disclosure further provides a method of producing new $V_H$ and $V_L$ domains and/or functional antibodies comprising all or a portion of such domains derived from the $V_H$ or $V_L$ domains of LOPD180.

Additional aspects of the disclosure will be set forth in part in the description which follows, and in part will be apparent from the description, or may be learned by practicing the invention. The invention is set forth and particularly pointed out in the appended claims, and the present disclosure should not be construed as limiting the scope of the claims in any way. The following detailed description includes exemplary representations of various embodiments of the invention, which are not restrictive of the invention, as claimed. The accompanying figures constitute a part of this specification and, together with the description, serve only to illustrate various embodiments and not limit the invention. Citation of references is not an admission that these references are prior art to the invention.

PD-1 (Programmed Death 1)

PD-1 (Programmed Death 1) is an inhibitory receptor and a counterpart of CTLA-4. This disclosure relates to modulation of immune responses mediated by the PD-1 receptor. PD-1 is a 50-55 kDa type I transmembrane receptor that was originally identified in a T cell line undergoing activation-induced apoptosis. PD-1 is expressed on T cells, B cells, and macrophages. The ligands for PD-1 are the B7 family members PD-L1 (B7-H1) and PD-L2 (B7-DC).

PD-1 is a member of the immunoglobulin (Ig) superfamily that contains a single Ig V-like domain in its extracellular region. The PD-1 cytoplasmic domain contains two tyrosines, with the most membrane-proximal tyrosine (VAYEEL in mouse PD-1) located within an ITIM (immuno-receptor tyrosine-based inhibitory motif). The presence of an ITIM on PD-1 indicates that this molecule functions to attenuate antigen receptor signaling by recruitment of cytoplasmic phosphatases. Human and murine PD-1 proteins share about 60% amino acid identity with conservation of four potential N-glycosylation sites, and residues that define the Ig-V domain. The ITIM in the cytoplasmic region and the ITIM-like motif surrounding the carboxy-terminal tyrosine (TEYATI in human and mouse) are also conserved between human and murine orthologues.

PD-1 is expressed on activated T cells, B cells, and monocytes. Experimental data implicates the interactions of PD-1 with its ligands in downregulation of central and peripheral immune responses. In particular, proliferation in wild-type T cells but not in PD-1-deficient T cells is inhibited in the presence of PD-L1. Additionally, PD-1-deficient mice exhibit an autoimmune phenotype. PD-1 deficiency in the C57BL/6 mice results in chronic progressive lupus-like glomerulonephritis and arthritis. In Balb/c mice, PD-1 deficiency leads to severe cardiomyopathy due to the presence of heart-tissue-specific self-reacting antibodies.

In general, a need exists to provide safe and effective therapeutic methods for immune disorders such as, for example, sepsis, autoimmune diseases, inflammatory disorders, allergies, transplant rejection, cancer, immune deficiency, and other immune system-related disorders. Modulation of the immune responses involved in these disorders can be accomplished by manipulation of the PD-1 pathway.

Programmed Cell Death 1 Ligand 1 (PD-L1)

Two forms of human PD-L1 molecules have been identified (Freeman et al. J. Exp. Med. 2000. 192:1027; Dong et al. 1999. Nature Medicine. 5: 1365). One form is a naturally occurring PD-L1 soluble polypeptide, i.e., having a short hydrophilic domain and no transmembrane domain, and is referred to herein as soluble PD-L1. The second form is a cell-associated polypeptide, i.e., having a transmembrane and cytoplasmic domain, referred to herein as PD-L1. PD-L2 molecules have also been identified. (Genbank Accession no. AF344424; Latchman et al. 2001. Nature Immunology. 2:1).

Anti-PD-1 Antibodies

The disclosure provides anti-PD-1 antibodies that comprise novel antigen-binding fragments. In a particular embodiment, the anti-PD1 antibody is LOPD180.

In general, antibodies can be made, for example, using traditional hybridoma techniques (Kohler and Milstein (1975) Nature, 256: 495-499), recombinant DNA methods (U.S. Pat. No. 4,816,567), or phage display performed with antibody, libraries (Clackson et al. (1991) Nature, 352: 624-628; Marks et al. (1991) J. Mol. Biol., 222: 581-597). For other antibody production techniques, see also Antibodies: A Laboratory Manual, eds. Harlow et al., Cold Spring Harbor Laboratory, 1988. The invention is not limited to any particular source, species of origin, method of production.

Intact antibodies, also known as immunoglobulins, are typically tetrameric glycosylated proteins composed of two light (L) chains of approximately 25 kDa each and two heavy (H) chains of approximately 50 kDa each. Two types of light chain, designated as the λ chain and the κ chain, are found in antibodies. Depending on the amino acid sequence of the constant domain of heavy chains, immunoglobulins can be assigned to five major classes: A, D, E, G, and M, and several of these may be further divided into subclasses (isotypes), e.g., $IgG_1$, $IgG_2$, $IgG_3$, $IgG_4$, $IgA_1$, and $IgA_2$.

The subunit structures and three-dimensional configurations of different classes of immunoglobulins are well known in the art. For a review of antibody structure, see Harlow et al., supra. Briefly, each light chain is composed of an N-terminal variable domain ($V_L$) and a constant domain ($C_L$). Each heavy chain is composed of an N-terminal variable domain ($V_H$), three or four constant domains ($C_H$), and a hinge region. The $C_H$ domain most proximal to $V_H$ is designated as $C_H1$. The $V_H$ and $V_L$ domains consist of four regions of relatively conserved sequence called framework regions (FR1, FR2, FR3, and FR4), which form a scaffold for three regions of hypervariable sequence called complementarity determining regions (CDRs). The CDRs contain most of the residues responsible for specific interactions with the antigen. The three CDRs are referred to as CDR1, CDR2, and CDR3. CDR constituents on the heavy chain are referred to as H1, H2, and H3, while CDR constituents on the light chain are referred to as L1, L2, and L3, accordingly. CDR3 and, particularly H3, are the greatest source of molecular diversity within the antigen-binding domain. H3, for example, can be as short as two amino acid residues or greater than 26.

The Fab fragment (Fragment antigen-binding) consists of the $V_H$-$C_H$1 and $V_L$—$C_L$ domains covalently linked by a disulfide bond between the constant regions. To overcome the tendency of non-covalently linked $V_H$ and $V_L$ domains in the Fv to dissociate when co-expressed in a host cell, a so-called single chain (sc) Fv fragment (scFv) can be constructed. In a scFv, a flexible and adequately long polypeptide links either the C-terminus of the $V_H$ to the N-terminus of the $V_L$ or the C-terminus of the $V_L$ to the N-terminus of the $V_H$. Most commonly, a 15-residue $(Gly_4Ser)_3$ peptide is used as a linker but other linkers are also known in the art.

Antibody diversity is a result of combinatorial assembly of multiple germline genes encoding variable regions and a variety of somatic events. The somatic events include recombination of variable gene segments with diversity (D) and joining (J) gene segments to make a complete $V_H$ region and the recombination of variable and joining gene segments to make a complete $V_L$ region. The recombination process itself is imprecise, resulting in the loss or addition of amino acids at the V(D)J junctions. These mechanisms of diversity occur in the developing B cell prior to antigen exposure. After antigenic stimulation, the expressed antibody genes in B cells undergo somatic mutation.

Based on the estimated number of germline gene segments, the random recombination of these segments, and random $V_H$-$V_L$ pairing, up to $1.6 \times 10^7$ different antibodies could be produced (Fundamental Immunology, 3rd ed., ed. Paul, Raven Press, New York, N.Y., 1993). When other processes which contribute to antibody diversity (such as somatic mutation) are taken into account, it is thought that upwards of $1 \times 10^{10}$ different antibodies could be potentially generated (Immunoglobulin Genes, $2^{nd}$ ed., eds. Jonio et al., Academic Press, San Diego, Calif., 1995). Because of the many processes involved in antibody diversity, it is highly unlikely that independently generated antibodies will have identical or even substantially similar amino acid sequences in the CDRs.

The disclosure provides novel CDRs derived from human immunoglobulin gene libraries. The structure for carrying a CDR will generally be an antibody heavy or light chain or a portion thereof, in which the CDR is located at a location corresponding to the CDR of naturally occurring $V_H$ and $V_L$. The structures and locations of immunoglobulin variable domains may be determined, for example, as described in Kabat et al., Sequences of Proteins of Immunological Interest, No. 91-3242, National Institutes of Health Publications, Bethesda, Md., 1991.

DNA and amino acid sequences of anti-PD-1 antibodies $V_H$ and $V_L$ domains are set forth below. Particular nonlimiting illustrative embodiments of the antibodies include LOPD180 and fragments and derivatives thereof.

```
PD-1 polypeptide sequence
LOCUS          NP_005009 288 aa linear
DEFINITION     programmed cell death protein 1 precursor [Homo sapiens].
ORIGIN
                                                              [SEQ ID NO: 1]
     1  mqipqapwpv vwavlqlgwr pgwfldspdr pwnpptfspa llvvtegdna tftcsfsnts 61  esfvinwyrm spsnqtdkla afpedrsqpg qdcrfrvtql pngrdfhmsv vrarrndsgt 121  ylcgaislap kaqikeslra elrvterrae vptahpspsp rpagqfqtiv vgvvggllgs 181  lvllvwvlav icsraargti garrtgqplk edpsavpvfs vdygeldfqw rektpeppvp 241  cvpeqteyat ivfpsgmgts sparrgsadg prsaqplrpe dghcswpl PD-1 nucleic acid sequence
LOCUS          NM_005018 2115 bp mRNA linear
DEFINITION     Homo sapiens programmed cell death 1 (PDCD1), mRNA.
ORIGIN
                                                              [SEQ ID NO: 2]
     1  agtttccctt ccgctcacct ccgcctgagc agtggagaag gcggcactct ggtggggctg 61  ctccaggcat gcagatccca caggcgccct ggccagtcgt ctgggcggtg ctacaactgg 121  gctggcggcc aggatggttc ttagactccc cagacaggcc ctggaacccc cccaccttct 181  ccccagccct gctcgtggtg accgaagggg acaacgccac cttcacctgc agcttctcca 241  acacatcgga gagcttcgtg ctaaactggt accgcatgag ccccagcaac cagacggaca 301  agctggccgc cttccccgag gaccgcagcc agcccggcca ggactgccgc ttccgtgtca 361  cacaactgcc caacgggcgt gacttccaca tgagcgtggt cagggcccgg cgcaatgaca 421  gcggcaccta cctctgtggg gccatctccc tggcccccaa ggcgcagatc aaagagagcc 481  tgcgggcaga gctcagggtg acagagagaa gggcagaagt gcccacagcc caccccagcc 541  cctcacccag gccagccggc cagttccaaa ccctggtggt tggtgtcgtg ggcggcctgc
```

-continued

```
 601  tgggcagcct ggtgctgcta gtctgggtcc tggccgtcat ctgctcccgg gccgcacgag
 661  ggacaatagg agccaggcgc accggccagc ccctgaagga ggacccctca gccgtgcctg
 721  tgttctctgt ggactatggg gagctggatt ccagtggcg agagaagacc ccggagcccc
 781  ccgtgcctg tgtccctgag cagacggagt atgccaccat tgtctttcct agcggaatgg
 841  gcacctcatc ccccgcccgc aggggctcag ctgacggccc tcggagtgcc cagccactga
 901  ggcctgagga tggacactgc tcttggcccc tctgaccggc ttccttggcc accagtgttc
 961  tgcagaccct ccaccatgag cccgggtcag cgcatttcct caggagaagc aggcagggtg
1021  caggccattg caggccgtcc aggggctgag ctgcctgggg gcgaccgggg ctccagcctg
1081  cacctgcacc aggcacagcc ccaccacagg actcatgtct caatgcccac agtgagccca
1141  ggcagcaggt gtcaccgtcc cctacaggga gggccagatg cagtcactgc ttcaggtcct
1201  gccagcacag agctgcctgc gtccagctcc ctgaatctct gctgctgctg ctgctgctgc
1261  tgctgctgcc tgccggcccgg ggctgaaggc gccgtggccc tgcctgacgc cccggagcct
1321  cctgcctgaa cttgggggct ggttggagat ggccttggag cagccaaggt gcccctggca
1381  gtggcatccc gaaacgccct ggacgcaggg cccaagactg gcacaggag tgggaggtac
1441  atggggctgg ggactcccca ggagttatct gctccctgca ggcctagaga agtttcaggg
1501  aaggtcagaa gagctcctgg ctgtggtggg cagggcagga aaccccctcca cctttacaca
1561  tgcccaggca gcacctcagg ccctttgtgg ggcagggaag ctgaggcagt aagcgggcag
1621  gcagagctgg aggcctttca ggcccagcca gcactctggc ctcctgccgc cgcattccac
1681  cccagcccct cacaccactc gggagaggga catcctacgg tcccaaggtc aggagggcag
1741  ggctggggtt gactcaggcc cctcccagct gtggccacct gggtgttggg agggcagaag
1801  tgcaggcacc tagggccccc catgtgccca ccctgggagc tctccttgga acccattcct
1861  gaaattattt aaaggggttg gccgggctcc caccagggcc tgggtgggaa ggtacaggcg
1921  ttcccccggg gcctagtacc ccgccgtgg cctatccact cctcacatcc acacactgca
1981  cccccactcc tggggcaggg ccaccagcat ccaggcggcc agcaggcacc tgagtggctg
2041  ggacaaggga tccccctccc ctgtggttct attatattat aattataatt aaatatgaga
2101  gcatgctaag gaaaa
```

PD-L1 polypeptide sequence
LOCUS         NP_001254635 176 aa linear
DEFINITION    programmed cell death 1 ligand 1 isoform b precursor
              [Homo sapiens].
ORIGIN
                                                                [SEQ ID NO: 3]

```
  1  mrifavfifm tywhllnapy nkingrilvv dpvtsehelt cqaegypkae viwtssdhqv
 61  lsgktttns  kreeklfnvt stlrintttn eifyctfrrl dpeenhtael vipelplahp
121  pnerthlvil gaillclgva ltfifrlrkg rmmdvkkcgi qdtnskkqsd thleet
```

PD-L1 nucleic acid sequence
LOCUS         NM_001267706 3349 bp mRNA linear
DEFINITION    Homo sapiens CD274 molecule (CD274), transcript variant 2,
              mRNA.
ORIGIN
                                                                [SEQ ID NO: 4]

```
  1  ggcgcaacgc tgagcagctg gcgcgtcccg cgcggcccca gttctgcgca gcttcccgag
 61  gctccgcacc agccgcgctt ctgtccgcct gcagggcatt ccagaaagat gaggatattt
121  gctgtcttta tattcatgac ctactggcat ttgctgaacg ccccatacaa caaaatcaac
181  caaagaattt tggttgtgga tccagtcacc tctgaacatg aactgacatg tcaggctgag
241  ggctacccca aggccgaagt catctggaca agcagtgacc atcaagtcct gagtggtaag
301  accaccacca ccaattccaa gagagaggag aagctttttca atgtgaccag cacactgaga
```

-continued

```
 361 atcaacacaa caactaatga gattttctac tgcactttta ggagattaga tcctgaggaa
 421 aaccatacag ctgaattggt catcccagaa ctacctctgg cacatcctcc aaatgaaagg
 481 actcacttgg taattctggg agccatctta ttatgccttg gtgtagcact gacattcatc
 541 ttccgtttaa gaaaagggag aatgatggat gtgaaaaaat gtggcatcca agatacaaac
 601 tcaaagaagc aaagtgatac acatttggag gagacgtaat ccagcattgg aacttctgat
 661 cttcaagcag ggattctcaa cctgtggttt aggggttcat cggggctgag cgtgacaaga
 721 ggaaggaatg ggcccgtggg atgcaggcaa tgtgggactt aaaaggccca agcactgaaa
 781 atggaacctg gcgaaagcag aggaggagaa tgaagaagaa tggagtcaaa cagggagcct
 841 ggagggagac cttgatactt tcaaatgcct gagggctca tcgacgcctg tgacagggag
 901 aaaggatact tctgaacaag gagcctccaa gcaaatcatc cattgctcat cctaggaaga
 961 cgggttgaga atccctaatt tgagggtcag ttcctgcaga agtgcccttt gcctccactc
1021 aatgcctcaa tttgttttct gcatgactga gagtctcagt gttggaacgg acagtatt
1081 atgtatgagt ttttcctatt tattttgagt ctgtgaggtc ttcttgtcat gtgagtgtgg
1141 ttgtgaatga tttcttttga agatatattg tagtagatgt tacaattttg tcgccaaact
1201 aaacttgctg cttaatgatt tgctcacatc tagtaaaaca tggagtattt gtaaggtgct
1261 tggtctcctc tataactaca agtatacatt ggaagcataa agatcaaacc gttggttgca
1321 taggatgtca cctttattta acccattaat actctggttg acctaatctt attctcagac
1381 ctcaagtgtc tgtgcagtat ctgttccatt taaatatcag ctttacaatt atgtggtagc
1441 ctacacacat aatctcattt catcgctgta accaccctgt tgtgataacc actattattt
1501 tacccatcgt acagctgagg aagcaaacag attaagtaac ttgcccaaac cagtaaatag
1561 cagacctcag actgccaccc actgtccttt tataatacaa tttacagcta tattttactt
1621 taagcaattc ttttattcaa aaaccattta ttaagtgccc ttgcaatatc aatcgctgtg
1681 ccaggcattg aatctacaga tgtgagcaag acaaagtacc tgtcctcaag gagctcatag
1741 tataatgagg agattaacaa gaaaatgtat tattacaatt tagtccagtg tcatagcata
1801 aggatgatgc gaggggaaaa cccgagcagt gttgccaaga ggaggaaata ggccaatgtg
1861 gtctgggacg gttggatata cttaaacatc ttaataatca gagtaatttt catttacaaa
1921 gagaggtcgg tacttaaaat aaccctgaaa ataacactg gaattccttt tctagcatta
1981 tatttattcc tgatttgcct ttgccatata atctaatgct tgtttatata gtgtctggta
2041 ttgtttaaca gttctgtctt ttctatttaa atgccactaa attttaaatt cataccttc
2101 catgattcaa aattcaaaag atcccatggg agatggttgg aaaatctcca cttcatcctc
2161 caagccattc aagtttcctt tccagaagca actgctactg cctttcattc atatgttctt
2221 ctaaagatag tctacatttg gaaatgtatg ttaaaagcac gtatttttaa aatttttttc
2281 ctaaatagta acacattgta tgtctgctgt gtactttgct atttttattt attttagtgt
2341 ttcttatata gcagatggaa tgaatttgaa gttcccaggg ctgaggatcc atgccttctt
2401 tgtttctaag ttatcttttcc catagctttt cattatcttt catatgatcc agtatatgtt
2461 aaatatgtcc tacatataca tttagacaac caccatttgt taagtatttg ctctaggaca
2521 gagtttggat tgtttatgt ttgctcaaaa ggagacccat gggctctcca gggtgcactg
2581 agtcaatcta gtcctaaaaa gcaatcttat tattaactct gtatgacaga atcatgtctg
2641 gaactttgt ttttctgcttt ctgtcaagta taaacttcac tttgatgctg tacttgcaaa
2701 atcacatttt ctttctggaa attccggcag tgtaccttga ctgctagcta ccctgtgcca
```

-continued

```
2761  gaaaagcctc attcgttgtg cttgaaccct tgaatgccac cagctgtcat cactacacag
2821  ccctcctaag aggcttcctg gaggtttcga gattcagatg ccctgggaga tcccagagtt
2881  tcctttccct cttggccata ttctggtgtc aatgacaagg agtaccttgg ctttgccaca
2941  tgtcaaggct gaagaaacag tgtctccaac agagctcctt gtgttatctg tttgtacatg
3001  tgcatttgta cagtaattgg tgtgacagtg ttctttgtgt gaattacagg caagaattgt
3061  ggctgagcaa ggcacatagt ctactcagtc tattcctaag tcctaactcc tccttgtggt
3121  gttggatttg taaggcactt tatccctttt gtctcatgtt tcatcgtaaa tggcataggc
3181  agagatgata cctaattctg catttgattg tcactttttg tacctgcatt aatttaataa
3241  aatattctta tttattttgt tacttggtac accagcatgt ccattttctt gtttattttg
3301  tgtttaataa aatgttcagt ttaacatccc agtggagaaa gttaaaaaa
```

PD-L2 polypeptide sequence
LOCUS         NP_079515      273 aa    linear
DEFINITION    programmed cell death 1 ligand 2 precursor [Homo sapiens].
ORIGIN
                                                                    [SEQ ID NO: 5]
```
  1 miflllmlsl elqlhqiaal ftvtvpkely iiehgsnvtl ecnfdtgshv nlgaitaslq
 61 kvendtsphr eratlleeql plgkasfhip qvqvrdegqy qciiiygvaw dykyltlkvk
121 asyrkinthi lkvpetdeve ltcqatgypl aevswpnvsv pantshsrtp eglyqvtsvl
181 rlkpppgrnf scvfwnthvr eltlasidlq sqmeprthpt wllhifipfc iiafifiatv
241 ialrkqlcqk lysskdttkr pvtttkrevn sai
```

PD-L2 nucleic acid sequence
LOCUS         NM_025239     2418 bp    mRNA    linear
DEFINITION    Homo sapiens programmed cell death 1 ligand 2 (PDCD1LG2),
              mRNA.
ORIGIN
                                                                    [SEQ ID NO: 6]
```
   1  gcaaacctta agctgaatga acaactttc ttctcttgaa tatatcttaa cgccaaattt
  61  tgagtgcttt tttgttaccc atcctcatat gtcccagcta gaaagaatcc tgggttggag
 121  ctactgcatg ttgattgttt tgttttcct tttggctgtt cattttggtg gctactataa
 181  ggaaatctaa cacaaacagc aactgttttt tgttgtttac ttttgcatct ttacttgtgg
 241  agctgtggca agtcctcata tcaaatacag aacatgatct tcctcctgct aatgttgagc
 301  ctggaattgc agcttcacca gatagcagct ttattcacag tgacagtccc taaggaactg
 361  tacataatag agcatggcag caatgtgacc ctggaatgca actttgacac tggaagtcat
 421  gtgaaccttg gagcaataac agccagtttg caaaaggtgg aaaatgatac atccccacac
 481  cgtgaaagag ccactttgct ggaggagcag ctgcccctag ggaaggcctc gttccacata
 541  cctcaagtcc aagtgaggga cgaaggacag taccaatgca taatcatcta tggggtcgcc
 601  tgggactaca gtacctgac tctgaaagtc aaagcttcct acaggaaaat aaacactcac
 661  atcctaaagg ttccagaaac agatgaggta gagctcacct gccaggctac aggttatcct
 721  ctggcagaag tatcctggcc aaacgtcagc gttcctgcca acaccagcca ctccaggacc
 781  cctgaaggcc tctaccaggt caccagtgtt ctgcgcctaa agccaccccc tggcagaaac
 841  ttcagctgtg tgttctggaa tactcacgtg agggaactta ctttggccag cattgacctt
 901  caaagtcaga tggaacccag gacccatcca acttggctgc ttcacatttt catccccttc
 961  tgcatcattg ctttcatttt catagccaca gtgatagccc taagaaaaca actctgtcaa
1021  aagctgtatt cttcaaagga cacaacaaaa agacctgtca ccacaacaaa gagggaagtg
1081  aacagtgcta tctgaacctg tggtcttggg agccagggtg acctgatatg acatctaaag
1141  aagcttctgg actctgaaca agaattcggt ggcctgcaga gcttgccatt tgcactttc
```

```
-continued
1201  aaatgccttt ggatgaccca gcactttaat ctgaaacctg caacaagact agccaacacc 1261  tggccatgaa acttgcccct tcactgatct ggactcacct ctggagccta tggctttaag 1321  caagcactac tgcactttac agaattaccc cactggatcc tggacccaca gaattccttc 1381  aggatccttc ttgctgccag actgaaagca aaggaatta tttcccctca gttttctaa 1441  gtgatttcca aaagcagagg tgtgtggaaa tttccagtaa cagaaacaga tgggttgcca 1501  atagagttat tttttatcta tagcttcctc tgggtactag aagaggctat tgagactatg 1561  agctcacaga cagggcttcg cacaaactca aatcataatt gacatgtttt atggattact 1621  ggaatcttga tagcataatg aagttgttct aattaacaga gagcatttaa atatacacta 1681  agtgcacaaa ttgtggagta aagtcatcaa gctctgtttt tgaggtctaa gtcacaaagc 1741  atttgtttta acctgtaatg gcaccatgtt taatggtggt tttttttttg aactacatct 1801  ttcctttaaa aattattggt ttcttttat ttgttttac cttagaaatc aattatatac 1861  agtcaaaaat atttgatatg ctcatacgtt gtatctgcag caatttcaga taagtagcta 1921  aaatggccaa agccccaaac taagcctcct tttctggccc tcaatatgac tttaaatttg 1981  acttttcagt gcctcagttt gcacatctgt aatacagcaa tgctaagtag tcaaggcctt 2041  tgataattgg cactatggaa atcctgcaag atcccactac atatgtgtgg agcagaaggg 2101  taactcggct acagtaacag cttaattttg ttaaatttgt tctttatact ggagccatga 2161  agctcagagc attagctgac ccttgaacta ttcaaatggg cacattagct agtataacag 2221  acttacatag gtgggcctaa agcaagctcc ttaactgagc aaaatttggg gcttatgaga 2281  atgaaagggt gtgaaattga ctaacagaca aatcatacat ctcagtttct caattctcat 2341  gtaaatcaga gaatgccttt aaagaataaa actcaattgt tattcttcaa cgttctttat 2401  atattctact tttgggta
```

LOPD180 heavy chain variable region polypeptide sequence
LOPD180_VH_AA
[SEQ ID NO: 7]
QVQLQESGPGLVKPSQTLSLTCTVSGGSISSGAYYWSWIRQHPGKGLEWIGYIYYNGNTYYNPSLRSRVTISVDTSK

NQFSLKLSSVTAADTAVYYCVRASDYVWGGYHYFDAFDLWGRGTLVTVSS

LOPD180 heavy chain variable region nucleic acid sequence
LOPD180_VH_DNA
[SEQ ID NO: 8]
CAGGTGCAGCTGCAGGAGTCGGGCCCAGGACTGGTGAAGCCTTCACAGACCCTGTCCCTCACCTGCACTGTCTCTGG

TGGCTCCATCAGCAGTGGTGCTTATTACTGGAGCTGGATCCGCCAGCACCCAGGGAAGGGCCTGGAGTGGATTGGGT

ACATCTATTACAATGGGAACACGTACTACAACCCGTCCCTCAGGAGTCGAGTTACCATATCAGTAGACACGTCTAAG

AACCAGTTCTCCCTGAAGCTGAGCTCTGTGACTGCCGCGGACACGGCCGTCTATTACTGTGTGAGAGCGTCTGATTA

CGTTTGGGGGGGTTATCATTATTTCGACGCGTTCGACCTCTGGGGCCGGGGAACCCTGGTCACCGTCTCCTCA

LOPD180 light chain variable region polypeptide sequence
LOPD180_VL_AA
[SEQ ID NO: 9]
QSVLTQPPSASGTPGQRVTISCSGSNSNIGSNSVNWYQQLPGTAPKLLIYGNNQRPSGVPDRFSGSKSGTSASLAIS

GLQSEDEADYYCAAWDDSLNGPVFGGGTKVTVL

LOPD180 light chain variable region nucleic acid sequence
LOPD180_VL_DNA
[SEQ ID NO: 10]
CAGTCTGTGCTGACTCAGCCACCCTCAGCGTCTGGGACCCCCGGGCAGAGGGTCACCATCTCTTGTTCTGGAAGCAA

CTCCAACATCGGAAGTAATTCTGTAAACTGGTACCAGCAGCTCCCAGGAACGGCCCCCAAACTCCTCATCTATGGTA

ATAATCAGCGGCCCTCAGGGGTCCCTGACCGATTCTCTGGCTCCAAGTCTGGCACCTCAGCCTCCCTGGCCATCAGT

GGGCTCCAGTCTGAGGATGAGGCTGATTATTACTGTGCAGCATGGGATGACAGCCTGAATGGTCCGGTATTCGGCGG

AGGGACCAAGGTCACCGTCCTA

```
LOPD180 heavy chain polypeptide sequence
LOPD180 HC pEU15.1-TM za allotype
Average Mass = 50087.4406, Monoisotopic Mass = 50055.8736
Modified amino acids: Pyr(J) = Pyroglutamic acid
                                                                   [SEQ ID NO: 11]
   1    JVQLQ ESGPG LVKPS QTLSL TCTVS GGSIS SGAYY WSWIR QHPGK GLEWI

51    GYIYY NGNTY YNPSL RSRVT ISVDT SKNQF SLKLS SVTAA DTAVY YCVRA

101    SDYVW GGYHY FDAFD LWGRG TLVTV SSAST KGPSV FPLAP SSKST SGGTA

151    ALGCL VKDYF PEPVT VSWNS GALTS GVHTF PAVLQ SSGLY SLSSV VTVPS

201    SSLGT QTYIC NVNHK PSNTK VDKKV EPKSC DKTHT CPPCP APEFE GGPSV

251    FLFPP KPKDT LMISR TPEVT CVVVD VSHED PEVKF NWYVD GVEVH NAKTK

301    PREEQ YNSTY RVVSV LTVLH QDWLN GKEYK CKVSN KALPA SIEKT ISKAK

351    GQPRE PQVYT LPPSR DELTK NQVSL TCLVK GFYPS DIAVE WESNG QPENN

401    YKTTP PVLDS DGSFF LYSKL TVDKS RWQQG NVFSC SVMHE ALHNH YTQKS

451    LSLSP G

LOPD180 light chain polypeptide sequence
LOPD180 LC
Modified amino acids: Pyr(J) = Pyroglutamic acid
                                                                   [SEQ ID NO: 12]
   1    JSVLT QPPSA SGTPG QRVTI SCSGS NSNIG SNSVN WYQQL PGTAP KLLIY

51    GNNQR PSGVP DRFSG SKSGT SASLA ISGLQ SEDEA DYYCA AWDDS LNGPV

101    FGGGT KVTVL GQPKA APSVT LFPPS SEELQ ANKAT LVCLI SDFYP GAVTV

151    AWKAD SSPVK AGVET TTPSK QSNNK YAASS YLSLT PEQWK SHRSY SCQVT

201    HEGST VEKTV APTEC S
```

In certain embodiments, the isolated antibody or antigen-binding fragment thereof binds to a PD-1 polypeptide and comprises a VH and/or a VL, where the VH and/or VL are each identical to or each have at least 90%, 95%, or 98% identity to the VH and VL amino acid sequences of SEQ ID NOs: 7 and 9.

In further embodiments, the isolated antibody or antigen-binding fragment thereof binds to a PD-1 polypeptide and comprises a VH region comprising the H1, H2 and H3 regions of LOPD180, where H1 corresponds to amino acids 31-37 of SEQ ID NO: 7, where H2 corresponds to amino acids 52-67 of SEQ ID NO: 7, and where H3 corresponds to amino acids 110-116 of SEQ ID NO: 7.

In further embodiments, the isolated antibody or antigen-binding fragment thereof binds to a PD-1 polypeptide and comprises a VL region comprising the L1, L2 and L3 regions of LOPD180, where L1 corresponds to amino acids 23-35 of SEQ ID NO: 9, where L2 corresponds to amino acids 51-57 of SEQ ID NO: 9, and where L3 corresponds to amino acids 90-100 of SEQ ID NO: 9.

In additional embodiments, the isolated antibody or antigen-binding fragment thereof binds to a PD-1 polypeptide and comprises a VH region and a VL region wherein the VH region comprises the H1, H2 and H3 regions of LOPD180, where H1 corresponds to amino acids 31-37 of SEQ ID NO: 7, where H2 corresponds to amino acids 52-67 of SEQ ID NO: 7, and where H3 corresponds to amino acids 110-116 of SEQ ID NO: 7.

In additional embodiments, the isolated antibody or antigen-binding fragment thereof binds to a PD-1 polypeptide and comprises a VH and a VL region where the VL region comprises the L1, L2 and L3 regions of LOPD180, where L1 corresponds to amino acids 23-35 of SEQ ID NO: 9, where L2 corresponds to amino acids 51-57 of SEQ ID NO: 9, and where L3 corresponds to amino acids 90-100 of SEQ ID NO: 9.

In particular embodiments, the isolated antibody or antigen-binding fragment thereof binds to a PD-1 polypeptide and comprises a VH and a VL region where the VH region comprises the H1, H2 and H3 regions of LOPD180, where H1 corresponds to amino acids 31-37 of SEQ ID NO: 7, where H2 corresponds to amino acids 52-67 of SEQ ID NO: 7, and where H3 corresponds to amino acids 110-116 of SEQ ID NO: 7 and the VL region comprises the L1, L2 and L3 regions of LOPD180, where L1 corresponds to amino acids 23-35 of SEQ ID NO: 9, where L2 corresponds to amino acids 51-57 of SEQ ID NO: 9, and where L3 corresponds to amino acids 90-100 of SEQ ID NO: 9.

In certain embodiments, the isolated antibody or antigen-binding fragment thereof binds to a PD-1 polypeptide and comprises a H3, where the H3 corresponds to amino acids 110-116 of SEQ ID NO: 7.

Anti-PD-1 antibodies may optionally comprise antibody constant regions or parts thereof. For example, a $V_L$ domain may have attached, at its C terminus, antibody light chain constant domains including human Cκ or Cλ, chains. Similarly, a specific antigen-binding domain based on a $V_H$ domain may have attached all or part of an immunoglobulin heavy chain derived from any antibody isotype, e.g., IgG, IgA, IgE, and IgM and any of the isotype sub-classes, which include but are not limited to, $IgG_1$ and $IgG_4$. In the exemplary embodiments, PD1-17, PD1-28, PD1-33, and PD1-35, antibodies comprise C-terminal fragments of heavy and light chains of human $IgG_{1\lambda}$, while PD1-F2 comprises C-terminal fragments of heavy and light chains of human $IgG_{1\kappa}$. The DNA and amino acid sequences for the C-terminal fragment of are well known in the art (see, e.g., Kabat et al., Sequences of Proteins of Immunological Interest, No. 91-3242, National Institutes of Health Publications, Bethesda, Md., 1991). Nonlimiting exemplary sequences are set forth in Table 4 of U.S. Pat. No. 7,488,802, which is herein incorporated by reference in its entirety.

Certain embodiments comprise a $V_H$ and/or $V_L$ domain of an Fv fragment from LOPD180. Further embodiments comprise at least one CDR of any of these $V_H$ and $V_L$ domains. Antibodies, comprising at least one of the CDR sequences set forth in Figure 1 are encompassed within the scope of this invention. An embodiment, for example, comprises an H3 fragment of the $V_H$ domain of antibodies chosen from LOPD180.

In certain embodiments, the $V_H$ and/or $V_L$ domains may be germlined, i.e., the framework regions (FRs) of these domains are mutated using conventional molecular biology techniques to match those produced by the germline cells. In other embodiments, the framework sequences remain diverged from the consensus germline sequences.

In certain embodiments, the antibodies specifically bind an epitope within the extracellular domain of human PD-1. The predicted extracellular domain consists of a sequence from about amino acid 21 to about amino acid 170 of PD-1 (Swissport Accession No. Q15116). In certain other embodiments, the antibodies specifically bind an epitope within the extracellular domain of mouse PD-1, with an affinity of more than $10^7 M^{-1}$, and preferably more than $10^8 M^{-1}$. The amino acid sequence of mouse PD-1 is set out forth at GenBank Accession No. NM_008798, and is as a whole about 60% identical to its human counterpart. In further embodiments, antibodies of the invention bind to the PD-L-binding domain of PD-1.

It is contemplated that antibodies of the invention may also bind with other proteins, including, for example, recombinant proteins comprising all or a portion of the PD-1 extracellular domain.

One of ordinary skill in the art will recognize that the antibodies of this invention may be used to detect, measure, and inhibit proteins that differ somewhat from PD-1. The antibodies are expected to retain the specificity of binding so long as the target protein comprises a sequence which is at least about 60%, 70%, 80%, 90%, 95%, or more identical to any sequence of at least 100, 80, 60, 40, or 20 of contiguous amino acids in the sequence set forth in SEQ ID NO:1. The percent identity is determined by standard alignment algorithms such as, for example, Basic Local Alignment Tool (BLAST) described in Altshul et al. (1990) J. Mol. Biol., 215: 403-410, the algorithm of Needleman et al. (1970) J. Mol. Biol., 48: 444-453, or the algorithm of Meyers et al. (1988) Comput. Appl. Biosci., 4: 11-17.

In addition to the sequence homology analyses, epitope mapping (see, e.g., Epitope Mapping Protocols, ed. Morris, Humana Press, 1996) and secondary and tertiary structure analyses can be carried out to identify specific 3D structures assumed by the disclosed antibodies and their complexes with antigens. Such methods include, but are not limited to, X-ray crystallography (Engstom (1974) Biochem. Exp. Biol., 11:7-13) and computer modeling of virtual representations of the presently disclosed antibodies (Fletterick et al. (1986) Computer Graphics and Molecular Modeling, in Current Communications in Molecular Biology, Cold Spring Harbor Laboratory, Cold Spring Harbor, N.Y.).

Derivatives

This disclosure also provides a method for obtaining an antibody specific for PD-1. CDRs in such antibodies are not limited to the specific sequences of $V_H$ and $V_L$ identified herein, and may include variants of these sequences that retain the ability to specifically bind PD-1. Such variants may be derived from the sequences listed herein by a skilled artisan using techniques well known in the art. For example, amino acid substitutions, deletions, or additions, can be made in the FRs and/or in the CDRs. While changes in the FRs are usually designed to improve stability and immunogenicity of the antibody, changes in the CDRs are typically designed to increase affinity of the antibody for its target. Variants of FRs also include naturally occurring immunoglobulin allotypes. Such affinity-increasing changes may be determined empirically by routine techniques that involve altering the CDR and testing the affinity antibody for its target. For example, conservative amino acid substitutions can be made within any one of the disclosed CDRs. Various alterations can be made according to the methods described in Antibody Engineering, $2^{nd}$ ed., Oxford University Press, ed. Borrebaeck, 1995. These include but are not limited to nucleotide sequences that are altered by the substitution of different codons that encode a functionally equivalent amino acid residue within the sequence, thus producing a "silent" change. For example, the nonpolar amino acids include alanine, leucine, isoleucine, valine, proline, phenylalanine, tryptophan, and methionine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Substitutes for an amino acid within the sequence may be selected from other members of the class to which the amino acid belongs (see Table 2). Furthermore, any native residue in the polypeptide may also be substituted with alanine (see, e.g., MacLennan et al. (1998) Acta Physiol. Scand. Suppl. 643:55-67; Sasaki et al. (1998) Adv. Biophys. 35:1-24).

TABLE 2

| Original Residues | Exemplary Substitutions | Typical Substitutions |
|---|---|---|
| Ala (A) | Val, Leu, Ile | Val |
| Arg (R) | Lys, Gln, Asn | Lys |
| Asn (N) | Gln | Gln |
| Asp (D) | Glu | Glu |
| Cys (C) | Ser, Ala | Ser |
| Gln (Q) | Asn | Asn |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1,4-Diamino-butyric Acid, Gln, Asn | Arg |
| Met (M) | Leu, Phe, Ile | Leu |
| Phe (F) | Leu, Val, Ile, Ala, Tyr | Leu |
| Pro (P) | Ala | Gly |
| Ser (S) | Thr, Ala, Cys | Thr |
| Thr (T) | Ser | Ser |
| Trp (W) | Tyr, Phe | Tyr |
| Tyr (Y) | Trp, Phe, Thr, Ser | Phe |
| Val (V) | Ile, Met, Leu, Phe, Ala, Norleucine | Leu |

Derivatives and analogs of antibodies of the invention can be produced by various techniques well known in the art, including recombinant and synthetic methods (Maniatis (1990) Molecular Cloning, A Laboratory Manual, $2^{nd}$ ed., Cold Spring Harbor Laboratory, Cold Spring Harbor, N.Y., and Bodansky et al. (1995) The Practice of Peptide Synthesis, $2^{nd}$ ed., Spring Verlag, Berlin, Germany).

In one embodiment, a method for making a $V_H$ domain which is an amino acid sequence variant of a $V_H$ domain of the invention comprises a step of adding, deleting, substituting, or inserting one or more amino acids in the amino acid sequence of the presently disclosed $V_H$ domain, optionally combining the $V_H$ domain thus provided with one or more $V_L$ domains, and testing the $V_H$ domain or $V_H/V_L$ combination or combinations for a specific binding to PD-1 or and, optionally, testing the ability of such antigen-binding domain to modulate PD-1 activity. The $V_L$ domain may have an amino acid sequence that is identical or is substantially to a polypeptide of the invention.

An analogous method can be employed in which one or more sequence variants of a $V_L$ domain disclosed herein are combined with one or more $V_H$ domains.

A further aspect of the disclosure provides a method of preparing antigen-binding fragment that specifically binds with PD-1. The method comprises:
  (a) providing a starting repertoire of nucleic acids encoding a $V_H$ domain that either includes a CDR3 to be replaced or lacks a CDR3 encoding region;
  (b) combining the repertoire with a donor nucleic acid encoding an amino acid sequence substantially as set out herein for a $V_H$ CDR3 (i.e., H3) such that the donor nucleic acid is inserted into the CDR3 region in the repertoire, so as to provide a product repertoire of nucleic acids encoding a $V_H$ domain;
  (c) expressing the nucleic acids of the product repertoire;
  (d) selecting a binding fragment specific for PD-1; and
  (e) recovering the specific binding fragment or nucleic acid encoding it.

Again, an analogous method may be employed in which a $V_L$ CDR3 (i.e., L3) of the invention is combined with a repertoire of nucleic acids encoding a $V_L$ domain, which either include a CDR3 to be replaced or lack a CDR3 encoding region.

A sequence encoding a CDR of the invention (e.g., CDR3) may be introduced into a repertoire of variable domains lacking the respective CDR (e.g., CDR3), using recombinant DNA technology, for example, using methodology described by Marks et al. (Bio/Technology (1992) 10: 779-783). In particular, consensus primers directed at or adjacent to the 5' end of the variable domain area can be used in conjunction with consensus primers to the third framework region of human $V_H$ genes to provide a repertoire of $V_H$ variable domains lacking a CDR3. The repertoire may be combined with a CDR3 of a particular antibody. Using analogous techniques, the CDR3-derived sequences may be shuffled with repertoires of $V_H$ or $V_L$ domains lacking a CDR3, and the shuffled complete $V_H$ or $V_L$ domains combined with a cognate $V_L$ or $V_H$ domain to make the PD-1-specific antibodies of the invention. The repertoire may then be displayed in a suitable host system such as the phage display system such as described in WO92/01047 so that suitable antigen-binding fragments can be selected.

Analogous shuffling or combinatorial techniques are also disclosed by Stemmer (Nature (1994) 370: 389-391), who describes the technique in relation to a β-lactamase gene but observes that the approach may be used for the generation of antibodies.

In further embodiments, one may generate novel $V_H$ or $V_L$ regions carrying one or more sequences derived from the sequences disclosed herein using random mutagenesis of one or more selected $V_H$ and/or $V_L$ genes. One such technique, error-prone PCR, is described by Gram et al. (Proc. Nat. Acad. Sci. U.S.A. (1992) 89: 3576-3580).

Another method that may be used is to direct mutagenesis to CDRs of $V_H$ or $V_L$ genes. Such techniques are disclosed by Barbas et al. (Proc. Nat. Acad. Sci. U.S.A. (1994) 91: 3809-3813) and Schier et al. (J. Mol. Biol. (1996) 263: 551-567).

Similarly, one or more, or all three CDRs may be grafted into a repertoire of $V_H$ or $V_L$ domains, which are then screened for an antigen-binding fragment specific for PD-1.

A portion of an immunoglobulin variable domain will comprise at least one of the CDRs substantially as set out herein and, optionally, intervening framework regions from the scFv fragments as set out herein. The portion may include at least about 50% of either or both of FR1 and FR4, the 50% being the C-terminal 50% of FR1 and the N-terminal 50% of FR4. Additional residues at the N-terminal or C-terminal end of the substantial part of the variable domain may be those not normally associated with naturally occurring variable domain regions. For example, construction of antibodies by recombinant DNA techniques may result in the introduction of N- or C-terminal residues encoded by linkers introduced to facilitate cloning or other manipulation steps. Other manipulation steps include the introduction of linkers to join variable domains to further protein sequences including immunoglobulin heavy chain constant regions, other variable domains (for example, in the production of diabodies), or proteinaceous labels as discussed in further detail below.

Although the embodiments illustrated in the Examples comprise a "matching" pair of $V_H$ and $V_L$ domains, a skilled artisan will recognize that alternative embodiments may comprise antigen-binding fragments containing only a single CDR from either $V_L$ or $V_H$ domain. Either one of the single chain specific binding domains can be used to screen for complementary domains capable of forming a two-domain specific antigen-binding fragment capable of, for example, binding to PD-1. The screening may be accomplished by phage display screening methods using the so-called hierarchical dual combinatorial approach disclosed in WO92/01047, in which an individual colony containing either an H or L chain clone is used to infect a complete library of clones encoding the other chain (L or H) and the resulting two-chain specific binding domain is selected in accordance with phage display techniques as described.

Anti-PD1 antibodies described herein can be linked to another functional molecule, e.g., another peptide or protein (albumin, another antibody, etc.), toxin, radioisotope, cytotoxic or cytostatic agents. For example, the antibodies can be linked by chemical cross-linking or by recombinant methods. The antibodies may also be linked to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192; or 4,179,337. The antibodies can be chemically modified by covalent conjugation to a polymer, for example, to increase their circulating half-life. Exemplary polymers and methods to attach them are also shown in U.S. Pat. Nos. 4,766,106; 4,179,337; 4,495,285, and 4,609,546.

The disclosed antibodies may also be altered to have a glycosylation pattern that differs from the native pattern. For example, one or more carbohydrate moieties can be deleted and/or one or more glycosylation sites added to the original antibody. Addition of glycosylation sites to the presently disclosed antibodies may be accomplished by altering the amino acid sequence to contain glycosylation site consensus sequences known in the art. Another means of increasing the number of carbohydrate moieties on the antibodies is by chemical or enzymatic coupling of glycosides to the amino acid residues of the antibody. Such methods are described in WO 87/05330 and in Aplin et al. (1981) CRC Crit. Rev. Biochem., 22: 259-306. Removal of any carbohydrate moieties from the antibodies may be accomplished chemically or enzymatically, for example, as described by Hakimuddin et al. (1987) Arch. Biochem. Biophys., 259: 52; and Edge et al. (1981) Anal. Biochem., 118: 131 and by Thotakura et al. (1987) Meth. Enzymol., 138: 350. The antibodies may also be tagged with a detectable, or functional, label. Detectable labels include radiolabels such as $^{131}$I or $^{99}$Tc, which may also be attached to antibodies using conventional chemistry. Detectable labels also include enzyme labels such as horseradish peroxidase or alkaline phosphatase. Detectable labels further include chemical moieties such as biotin, which may be detected via binding to a specific cognate detectable moiety, e.g., labeled avidin.

Typically, an amino acid is substituted by a related amino acid having similar charge, hydrophobic, or stereochemical characteristics. Such substitutions would be within the ordinary skills of an artisan. Unlike in CDRs, more substantial changes can be made in FRs without adversely affecting the binding properties of an antibody. Changes to FRs include, but are not limited to, humanizing a non-human derived or engineering certain framework residues that are important for antigen contact or for stabilizing the binding site, e.g., changing the class or subclass of the constant region, changing specific amino acid residues which might alter the effector function such as Fc receptor binding, e.g., as described in U.S. Pat. Nos. 5,624,821 and 5,648,260 and Lund et al. (1991) J. Immun. 147: 2657-2662 and Morgan et al. (1995) Immunology 86: 319-324, or changing the species from which the constant region is derived.

One of skill in the art will appreciate that the modifications described above are not all-exhaustive, and that many other modifications would obvious to a skilled artisan in light of the teachings of the present disclosure.

Nucleic Acids, Cloning and Expression Systems

The present disclosure further provides isolated nucleic acids encoding the disclosed antibodies. The nucleic acids may comprise DNA or RNA and may be wholly or partially synthetic or recombinant. Reference to a nucleotide sequence as set out herein encompasses a DNA molecule with the specified sequence, and encompasses a RNA molecule with the specified sequence in which U is substituted for T, unless context requires otherwise.

The nucleic acids provided herein comprise a coding sequence for a CDR, a $V_H$ domain, and/or a $V_L$ domain disclosed herein.

The present disclosure also provides constructs in the form of plasmids, vectors, phagemids, transcription or expression cassettes which comprise at least one nucleic acid encoding a CDR, a $V_H$ domain, and/or a $V_L$ domain disclosed herein.

The disclosure further provides a host cell which comprises one or more constructs as above.

Also provided are nucleic acids encoding any CDR (H1, H2, H3, L1, L2, or L3), $V_H$ or $V_L$ domain, as well as methods of making of the encoded products. The method comprises expressing the encoded product from the encoding nucleic acid. Expression may be achieved by culturing under appropriate conditions recombinant host cells containing the nucleic acid. Following production by expression a $V_H$ or $V_L$ domain, or specific binding member may be isolated and/or purified using any suitable technique, then used as appropriate.

Antigen-binding fragments, $V_H$ and/or $V_L$ domains and encoding nucleic acid molecules and vectors may be isolated and/or purified from their natural environment, in substantially pure or homogeneous form, or, in the case of nucleic acid, free or substantially free of nucleic acid or genes of origin other than the sequence encoding a polypeptide with the required function.

Systems for cloning and expression of a polypeptide in a variety of different host cells are well known in the art. For cells suitable for producing antibodies, see Gene Expression Systems, Academic Press, eds. Fernandez et al., 1999. Briefly, suitable host cells include bacteria, plant cells, mammalian cells, and yeast and baculovirus systems. Mammalian cell lines available in the art for expression of a heterologous polypeptide include Chinese hamster ovary cells, HeLa cells, baby hamster kidney cells, NS0 mouse myeloma cells, and many others. A common bacterial host is E. coli. Any protein expression system compatible with the invention may be used to produce the disclosed antibodies. Suitable expression systems include transgenic animals described in Gene Expression Systems, Academic Press, eds. Fernandez et al., 1999.

Suitable vectors can be chosen or constructed, so that they contain appropriate regulatory sequences, including promoter sequences, terminator sequences, polyadenylation sequences, enhancer sequences, marker genes and other sequences as appropriate. Vectors may be plasmids or viral, e.g., phage, or phagemid, as appropriate. For further details see, for example, Sambrook et al., Molecular Cloning: A Laboratory Manual, 2nd ed., Cold Spring Harbor Laboratory Press, 1989. Many known techniques and protocols for manipulation of nucleic acid, for example, in preparation of nucleic acid constructs, mutagenesis, sequencing, introduction of DNA into cells and gene expression, and analysis of proteins, are described in detail in Current Protocols in Molecular Biology, 2nd Edition, eds. Ausubel et al., John Wiley & Sons, 1992.

A further aspect of the disclosure provides a host cell comprising a nucleic acid as disclosed here. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g., vaccinia or, for insect cells, baculovirus. For bacterial cells, suitable techniques may include calcium chloride transformation, electroporation and transfection using bacteriophage. The introduction of the nucleic acid into the cells may be followed by causing or allowing expression from the nucleic acid, e.g., by culturing host cells under conditions for expression of the gene.

Methods of Use

The disclosed anti-PD-1 antibodies are capable of negatively regulating PD-1-associated immune responses. In particular embodiments, the immune response is TcR/CD28-mediated. The disclosed antibodies can act as either agonists or antagonists of PD-1-associated immune responses, depending on the method of their use. The antibodies can be used to prevent, diagnose, or treat medical disorders in mammals, especially, in humans. Antibodies of the invention can also be used for isolating PD-1 or PD-1-expressing cells. Furthermore, the antibodies can be used to treat a subject at risk of or susceptible to a disorder or having a disorder associated with aberrant PD-1 expression or function.

Antibodies of the invention can be used in methods for induction of tolerance to a specific antigen (e.g., a therapeutic protein). In one embodiment, tolerance is induced against a specific antigen by co-administration of antigen and an anti-PD-1 antibody of the invention. For example, patients that received Factor VIII frequently generate antibodies to this protein; co-administration of an anti-PD-1 antibody of the invention in combination with recombinant Factor VIII is expected to result in the downregulation of immune responses to this clotting factor.

Antibodies of the invention can be used in circumstances where a reduction in the level of immune response may be desirable, for example, in certain types of allergy or allergic reactions (e.g., by inhibition of IgE production), autoimmune diseases (e.g., rheumatoid arthritis, type I diabetes mellitus, multiple sclerosis, inflammatory bowel disease, Crohn's disease, and systemic lupus erythematosus), tissue, skin and organ transplant rejection, and graft-versus-host disease (GVHD).

When diminished immune response is desirable, the anti-PD-1 antibodies of the invention may be used as agonists to PD-1 in order to enhance the PD-1-associated attenuation of the immune response. In these embodiments, co-presentation and physical proximity between positive (i.e., mediated by an antigen receptor, e.g., TcR or BcR) and negative (i.e., PD-1) signals are required. The preferred distance is less than or comparable to the size of a naturally occurring antigen-presenting cell, i.e., less than about 100 μm; more preferably, less than about 50 μm; and most preferably, less than about 20 μm.

In some embodiments, the positive (activating) and the negative (inhibiting) signals are provided by a ligand or antibodies immobilized on solid support matrix, or a carrier. In various embodiments, the solid support matrix may be composed of polymer such as activated agarose, dextran, cellulose, polyvinylidene fluoride (PVDF). Alternatively, the solid support matrix may be based on silica or plastic polymers, e.g., as nylon, dacron, polystyrene, polyacrylates, polyvinyls, teflons, etc.

The matrix can be implanted into the spleen of a patient. Alternatively, the matrix may be used for the ex vivo incubation of T cells obtained from a patient, which are then separated and implanted back into the patient. The matrix may also be made from a biodegradable material such as polyglycolic acid, polyhydroxyalkanoate, collagen, or gelatin so that they can be injected into the patient's peritoneal cavity, and dissolve after some time following the injection. The carrier can be shaped to mimic a cell (e.g., bead or microsphere).

In some embodiments, the positive signal is delivered by a T-cell-activating anti-CD3 antibody, which binds TcR. Activating anti-CD3 antibodies are known in the art (see, for example, U.S. Pat. Nos. 6,405,696 and 5,316,763). The ratio between the activating TcR signal and negative PD-1 signal is determined experimentally using conventional procedures known in the art or as described in Examples 8, 9, and 10.

Under certain circumstances, it may be desirable to elicit or enhance a patient's immune response in order to treat an immune disorder or cancer. The disorders being treated or prevented by the disclosed methods include but are not limited to infections with microbes (e.g. bacteria), viruses (e.g., systemic viral infections such as influenza, viral skin diseases such as herpes or shingles), or parasites; and cancer (e.g., melanoma and prostate cancers).

Stimulation of T cell activation with anti-PD-1 antibodies enhances T-T cell responses. In such cases, antibodies act as antagonists of PD-1. Thus, in some embodiments, the antibodies can be used to inhibit or reduce the downregulatory activity associated with PD-1, i.e., the activity associated with downregulation of TcR/CD28-mediated immune response. In these embodiments, the antibodies are not coupled to a positive signal such as the TcR-mediated stimulation, e.g., the antibodies are in their soluble, support-unbound, form. As demonstrated in the Examples, a blockade of PD-1/PD-L interaction with antagonizing anti-PD-1 antibodies leads to enhanced T cell proliferative responses, consistent with a downregulatory role for the PD-1 pathway in T-T interactions. In various embodiments, the antibodies inhibit binding of PD-L to PD-1 with an IC50 of less than 10 nM, and more preferably less then 5 nM, and most preferably less than 1 nM Inhibition of PD-L binding can be measured as described in Example 6 or using techniques known in the art.

The antibodies or antibody compositions of the present invention are administered in therapeutically effective amounts. Generally, a therapeutically effective amount may vary with the subject's age, condition, and sex, as well as the severity of the medical condition of the subject. A therapeutically effective amount of antibody ranges from about 0.001 to about 30 mg/kg body weight, preferably from about 0.01 to about 25 mg/kg body weight, from about 0.1 to about 20 mg/kg body weight, or from about 1 to about 10 mg/kg. The dosage may be adjusted, as necessary, to suit observed effects of the treatment. The appropriate dose is chosen based on clinical indications by a treating physician.

The antibodies may given as a bolus dose, to maximize the circulating levels of antibodies for the greatest length of time after the dose. Continuous infusion may also be used after the bolus dose.

Immune cells (e.g., activated T cells, B cells, or monocytes) can also be isolated from a patient and incubated ex vivo with antibodies of the invention. In some embodiments, immune responses can be inhibited by removing immune cells from a subject, contacting the immune cells in vitro with an anti-PD-1 antibody of the invention concomitantly with activation of the immune cells (e.g., by antibodies to the TcR and/or BcR antigen receptor). In such embodiments, the anti-PD-1 antibody should be used in a multivalent form such that PD-1 molecules on the surface of an immune cell become "crosslinked" upon binding to such antibodies. For example, the anti-PD-1 antibodies can be bound to solid support, such as beads, or crosslinked via a secondary antibody. The immune cells may be then isolated using methods known in the art and reimplanted into the patient.

In another aspect, the antibodies of the invention can be used as a targeting agent for delivery of another therapeutic or a cytotoxic agent (e.g., a toxin) to a cell expressing PD-1. The method includes administering an anti-PD-1 antibody coupled to a therapeutic or a cytotoxic agent or under conditions that allow binding of the antibody to PD-1.

The antibodies of the invention may also be used to detect the presence of PD-1 in biological samples. The amount of PD-1 detected may be correlated with the expression level of PD-1, which, in turn, is correlated with the activation status of immune cells (e.g., activated T cells, B cells, and monocytes) in the subject.

Detection methods that employ antibodies are well known in the art and include, for example, ELISA, radioimmunoassay, immunoblot, Western blot, immunofluorescence, immunoprecipitation. The antibodies may be provided in a diagnostic kit that incorporates one or more of these techniques to detect PD-1. Such a kit may contain other components, packaging, instructions, or other material to aid the detection of the protein.

Where the antibodies are intended for diagnostic purposes, it may be desirable to modify them, for example, with a ligand group (such as biotin) or a detectable marker group (such as a fluorescent group, a radioisotope or an enzyme).

If desired, the antibodies of the invention may be labeled using conventional techniques. Suitable detectable labels include, for example, fluorophores, chromophores, radioactive atoms, electron-dense reagents, enzymes, and ligands having specific binding partners. Enzymes are typically detected by their activity. For example, horseradish peroxidase can be detected by its ability to convert tetramethylbenzidine (TMB) to a blue pigment, quantifiable with a spectrophotometer. For detection, suitable binding partners include, but are not limited to, biotin and avidin or streptavidin, IgG and protein A, and the numerous receptor-ligand couples known in the art. Other permutations and possibilities will be readily apparent to those of ordinary skill in the art, and are considered as equivalents within the scope of the instant invention.

Antibodies of the invention can be used in screening methods to identify inhibitors of the PD-1 pathway effective as therapeutics. In such a screening assay, a first binding mixture is formed by combining PD-1 and an antibody of the invention; and the amount of binding in the first binding mixture (M0) is measured. A second binding mixture is also formed by combining PD-1, the antibody, and the compound or agent to be screened, and the amount of binding in the second binding mixture (M1) is measured. A compound to be tested may be another anti-PD-1 antibody, as illustrated in the Examples. The amounts of binding in the first and second binding mixtures are then compared, for example, by calculating the M1/M0 ratio. The compound or agent is considered to be capable of modulating a PD-1-associated downregulation of immune responses if a decrease in binding in the second binding mixture as compared to the first binding mixture is observed. The formulation and optimization of binding mixtures is within the level of skill in the art, such binding mixtures may also contain buffers and salts necessary to enhance or to optimize binding, and additional control assays may be included in the screening assay of the invention. Compounds found to reduce the PD-1-antibody binding by at least about 10% (i.e., M1/M0<0.9), preferably greater than about 30% may thus be identified and then, if desired, secondarily screened for the capacity to ameliorate a disorder in other assays or animal models as described below. The strength of the binding between PD-1 and an antibody can be measured using, for example, an enzyme-linked immunoadsorption assay (ELISA), radio-immunoassay (RIA), surface plasmon resonance-based technology (e.g., Biacore), all of which are techniques well known in the art.

The compound may then be tested in vitro as described in the Examples or in an animal model (see, generally, Immunologic Defects in Laboratory Animals, eds. Gershwin et al., Plenum Press, 1981), for example, such as the following: the SWR X NZB (SNF1) transgenic mouse model (Uner et al. (1998) J. Autoimmune. 11 (3): 233-240), the KRN transgenic mouse (K/BxN) model (Ji et al. (1999) Immunol. Rev. 169: 139); NZB X NZW (B/W) mice, a model for SLE (Riemekasten et al. (2001) Arthritis Rheum., 44(10): 2435-2445); experimental autoimmune encephalitis (EAE) in mouse, a model for multiple sclerosis (Tuohy et al. (1988) J. Immunol. 141: 1126-1130, Sobel et al. (1984) J. Immunol. 132: 2393-2401, and Traugott, Cell Immunol. (1989) 119: 114-129); the NOD mouse model of diabetes (Baxter et al. (1991) Autoimmunity, 9(1): 61-67), etc.).

Preliminary doses as, for example, determined according to animal tests, and the scaling of dosages for human administration is performed according to art-accepted practices. Toxicity and therapeutic efficacy can be determined by standard pharmaceutical procedures in cell cultures or experimental animals. The data obtained from the cell culture assays or animal studies can be used in formulating a range of dosage for use in humans. Therapeutically effective dosages achieved in one animal model can be converted for use in another animal, including humans, using conversion factors known in the art (see, e.g., Freireich et al. (1966) Cancer Chemother. Reports, 50(4): 219-244).

Pharmaceutical Compositions and Methods of Administration

The disclosure provides compositions comprising anti-PD-1 antibodies. Such compositions may be suitable for pharmaceutical use and administration to patients. The compositions typically comprise one or more antibodies of the present invention and a pharmaceutically acceptable excipient. The phrase "pharmaceutically acceptable excipient" includes any and all solvents, dispersion media, coatings, antibacterial agents and antifungal agents, isotonic agents, and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions. The pharmaceutical compositions may also be included in a container, pack, or dispenser together with instructions for administration.

A pharmaceutical composition of the invention is formulated to be compatible with its intended route of administration. Methods to accomplish the administration are known to those of ordinary skill in the art. The administration may, for example, be intravenous, intraperitoneal, intramuscular, intracavity, subcutaneous or transdermal. It may also be possible to obtain compositions which may be topically or orally administered, or which may be capable of transmission across mucous membranes.

Solutions or suspensions used for intradermal or subcutaneous application typically include one or more of the following components: a sterile diluent such as water for injection, saline solution, fixed oils, polyethylene glycols, glycerin, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. The pH can be adjusted with acids or bases, such as hydrochloric acid or sodium hydroxide. Such preparations may be enclosed in ampoules, disposable syringes or multiple dose vials made of glass or plastic.

Pharmaceutical compositions suitable for injection include sterile aqueous solutions or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars; polyalcohols such as mannitol, sorbitol, and sodium chloride in the composition. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and/or by the use of surfactants. Prolonged absorption of the injectable compositions can be brought about by including in the composition an agent which delays absorption, for example, aluminum monostearate, and gelatin.

Oral compositions generally include an inert diluent or an edible carrier. They can be enclosed in gelatin capsules or compressed into tablets. For oral administration, the antibodies can be combined with excipients and used in the form of tablets, troches, or capsules. Pharmaceutically compatible binding agents, and/or adjuvant materials can be included as part of the composition. The tablets, pills, capsules, troches, and the like can contain any of the following ingredients, or compounds of a similar nature; a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, detergents, bile salts, and fusidic acid derivatives. Transmucosal administration may be accomplished, for example, through the use of lozenges, nasal sprays, inhalers, or suppositories. For example, in case of antibodies that comprise the Fc portion, compositions may be capable of transmission across mucous membranes in intestine, mouth, or lungs (e.g., via the FcRn receptor-mediated pathway as described in U.S. Pat. No. 6,030,613). For transdermal administration, the active compounds may be formulated into ointments, salves, gels, or creams as generally known in the art. For administration by inhalation, the antibodies may be delivered in the form of an aerosol spray from pressured container or dispenser, which contains a suitable propellant, e.g., a gas such as carbon dioxide, or a nebulizer.

In certain embodiments, the presently disclosed antibodies are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions containing the presently disclosed antibodies can also be used as pharmaceutically acceptable carriers. These can be prepared according to methods known to those skilled in the art, for example, as described in U.S. Pat. No. 4,522,811.

It may be advantageous to formulate oral or parenteral compositions in a dosage unit form for ease of administration and uniformity of dosage. The term "dosage unit form" as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of the composition of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferred.

For any composition used in the present invention, the therapeutically effective dose can be estimated initially from cell culture assays. Examples of suitable bioassays include DNA replication assays, cytokine release assays, transcription-based assays, PD-1/PD-L1 binding assays, creatine kinase assays, assays based on the differentiation of pre-adipocytes, assays based on glucose uptake in adipocytes, immunological assays other assays as, for example, described in the Examples. The data obtained from the cell culture assays and animal studies can be used in formulating a range of dosage for use in humans. A dose may be formulated in animal models to achieve a circulating plasma concentration range that includes the $IC_{50}$ (i.e., the concentration of the antibody which achieves a half-maximal inhibition of symptoms). Circulating levels in plasma may be measured, for example, by high performance liquid chromatography. The effects of any particular dosage can be monitored by a suitable bioassay. The dosage lies preferably within a range of circulating concentrations with little or no toxicity. The dosage may vary depending upon the dosage form employed and the route of administration utilized.

Kits

The invention provides kits for the treatment or prevention of an immune response. In one embodiment, the kit includes a therapeutic or prophylactic composition containing an effective amount of an inhibitory anti-PD1 antibody that disrupts the biological activity of a PD1 and/or PD-L1 polynucleotide or polypeptide in unit dosage form. In another embodiment, the kit includes a therapeutic or prophylactic composition containing an effective amount of the anti-PD1 antibody LOPD180 in unit dosage form.

In some embodiments, the kit comprises a sterile container which contains a therapeutic or prophylactic cellular composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired an antibody or agent of the invention is provided together with instructions for administering the antibody or agent to a subject having or at risk of developing an immune disorder (e.g., a disorder associated with aberrant PD-1 expression or function). The instructions will generally include information about the use of the composition for the treatment or prevention of an immune disorder. In other embodiments, the instructions include at least one of the following: description of the therapeutic agent; dosage schedule and administration for treatment or prevention of an immune disorder or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the anti-PD1 antibodies in assay, screening, and therapeutic methods of the invention, and are not intended to limit the scope of what the inventors regard as their invention.

EXAMPLES

Example 1: Identification and Characterization of Anti-PD-1 Antibody, LOPD180

The invention provides the amino acid and nucleic acid sequences of an exemplary anti-PD1 antibody, LOPD180 light chain, heavy chain, light chain variable region, and heavy chain variable region as set forth above.

The identified antibody shows superior binding and inhibitory characteristics relative to other PD1 antibodies known in the art, for example relative to the PD-1 35 parent antibody as shown below in Table 1. Characteristics of the PD-1 35 parent antibody are also described in U.S. Pat. No. 7,488,802, which is herein incorporated by reference in its entirety.

| | PD1/PD-L1 ligand inhibition (nM) | | | | | | | | | | |
|---|---|---|---|---|---|---|---|---|---|---|---|
| | Human PD1 | | | | Cynomolgous PD1 | | | | Mouse PD1 | | |
| | GeoMean | lower 95% CL | upper 95% CL | n | GeoMean | lower 95% CL | upper 95% CL | n | GeoMean | lower 95% CL | upper 95% CL | n |
| PD1-35 parent | 0.838 | 0.467 | 1.5 | 2 | 1.07 | 0.306 | 3.74 | 2 | 28.5 | 1.12 | 728 | 2 |
| Germ_Lopd 180 | 0.0328 | 0.000694 | 1.55 | 2 | 0.103 | 0.0455 | 0.234 | 2 | 4.38 | 1.28 | 15 | 2 |

| | PD1/PD-L2 ligand inhibition (nM) | | | | Biacore Human PD1 | | |
|---|---|---|---|---|---|---|---|
| | Human PD1 | | | | | | |
| | GeoMean | lower 95% CL | upper 95% CL | n | Kd (nM) | kon (M-1s-1) | koff (s-1) |
| PD1-35 parent | 3.86 | 1.64 | 9.08 | 2 | >1000 nM | | |
| Germ_Lopd 180 | 0.0657 | 0.0516 | 0.0837 | 2 | 25 | 5.6E+05 | 1.4E-02 |

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents, publications, and accession numbers mentioned in this specification are herein incorporated by reference to the same extent as if each independent patent, publication, and accession number was specifically and individually indicated to be incorporated by reference.

What is claimed is:

1. An isolated antibody or antigen-binding fragment thereof comprising: a $V_H$ domain comprising SEQ ID NO: 7 and a $V_L$ domain comprising SEQ ID NO: 9.

2. The isolated antibody or antigen-binding fragment thereof of claim 1 that specifically binds an epitope within the extracellular domain of human or mouse PD-1.

3. The isolated antibody or antigen-binding fragment thereof of claim 1, wherein the antibody is an antigen binding fragment Fab, F(ab')2, Fv, scFv, Fd or dAb.

4. The isolated antibody or antigen-binding fragment thereof of claim 1, wherein the antibody specifically binds to the extracellular domain of PD-1 with an affinity constant greater than $10^7$ M$^{-1}$.

5. The isolated antibody or antigen-binding fragment thereof of claim 1, where the antibody inhibits the binding of PD-L1 or PD-L2 to PD-1 with an IC$_{50}$ of less than 10 nM.

6. The isolated antibody or antigen-binding fragment thereof of claim 1, wherein the antibody is a human antibody.

7. The isolated antibody or antigen-binding fragment thereof claim 1, wherein the antibody is IgG$_1$ or IgG$_4$.

8. The isolated antibody or antigen-binding fragment thereof of claim 1, wherein the antibody is IgG$_{1\lambda}$ or IgG$_{1\kappa}$.

9. The isolated antibody or antigen-binding fragment thereof of claim 1, wherein the VH domain comprises CDR1, CDR2 and CDR3 regions, where CDR1 consists of amino acids 31-37 of SEQ ID NO: 7, where CDR2 consists of amino acids 52-67 of SEQ ID NO: 7, and where CDR3 consists of amino acids 110-116 of SEQ ID NO: 7 and the VL domain comprises CDR1, CDR2 and CDR3 regions, where CDR1 consists of amino acids 23-35 of SEQ ID NO: 9, where CDR2 consists of amino acids 51-57 of SEQ ID NO: 9, and where CDR3 consists of amino acids 90-100 of SEQ ID NO: 9.

10. A pharmaceutical composition comprising the isolated antibody or antigen-binding fragment thereof of claim 1.

11. A kit comprising the isolated antibody claim 1, and directions for the use of the antibody in an immunological assay.

\* \* \* \* \*